(12) United States Patent
Garcon et al.

(10) Patent No.: US 9,364,533 B2
(45) Date of Patent: Jun. 14, 2016

(54) POLYANIONIC POLYMER ADJUVANTS FOR HAEMOPHILUS INFLUENZAE B SACCHARIDE VACCINES

(71) Applicant: GLAXOSMITHKLINE BIOLOGICALS S.A., Rixensart (BE)

(72) Inventors: Nathalie Marie-Josephe Garcon, Rixensart (BE); Dominique Lemoine, Rixensart (BE); Florence Emilie Jeanne Francoise Wauters, Rixensart (BE)

(73) Assignee: GLAXOSMITHKLINE BIOLOGICALS S.A., Rixensart (BE)

( * ) Notice: Subject to any disclaimer, the term of this patent is extended or adjusted under 35 U.S.C. 154(b) by 0 days.

(21) Appl. No.: 14/509,448

(22) Filed: Oct. 8, 2014

(65) Prior Publication Data

US 2015/0037368 A1 Feb. 5, 2015

Related U.S. Application Data

(63) Continuation of application No. 13/919,024, filed on Jun. 17, 2013, now abandoned, which is a continuation of application No. 13/396,843, filed on Feb. 15, 2012, now abandoned, which is a continuation of application No. 12/785,809, filed on May 24, 2010, now Pat. No. 8,137,681, which is a continuation of application No. 10/560,513, filed as application No. PCT/EP2004/006426 on Jun. 14, 2004, now Pat. No. 8,007,818.

(30) Foreign Application Priority Data

Jun. 16, 2003 (GB) .................... 0313916.9

(51) Int. Cl.
*A61K 39/102* (2006.01)
*A61K 39/39* (2006.01)
*A61K 39/12* (2006.01)
*C12N 7/00* (2006.01)
*A61K 39/00* (2006.01)

(52) U.S. Cl.
CPC ............ *A61K 39/39* (2013.01); *A61K 39/0018* (2013.01); *A61K 39/102* (2013.01); *A61K 39/12* (2013.01); *C12N 7/00* (2013.01); *A61K 2039/5252* (2013.01); *A61K 2039/55* (2013.01); *A61K 2039/55505* (2013.01); *A61K 2039/6037* (2013.01); *A61K 2039/70* (2013.01); *C12N 2730/10134* (2013.01); *C12N 2760/16233* (2013.01); *C12N 2770/32634* (2013.01)

(58) Field of Classification Search
None
See application file for complete search history.

(56) References Cited

U.S. PATENT DOCUMENTS 6,333,036 B1  12/2001  Arminjon et al.

FOREIGN PATENT DOCUMENTS

| WO | 98/17310 | 4/1998 |
|---|---|---|
| WO | 00/32239 | 6/2000 |
| WO | 01/66149 | 9/2001 |
| WO | 02/00249 | 1/2002 |

OTHER PUBLICATIONS

Konishi, et al., Effect of acidic polypeptides on aluminium toxicity in tube growth of pollen from tea (*Camellia sinensis* L.), Plant Sci 56(1): 55-59 (1988).
Liu, et al., Differential effects of poly (Glu<60>, Phe<40>) (GPhe) on murine TH1 and TH2 cells, Cellular Immunology 133(2): 420-433 (1991).
Esparza and Kissel, Parameters affecting the immunogenicity of microencapsulated tetanus toxoid. Vaccine, vol. 10(10): 714-720 (1992).
Watson and Davies, Influence of adjuvants on the immune response of sheep to a novel *Staphylococcus aureus* vaccine. Veterinary Microbiology, vol. 34: 139-153 (1993).
Rinella, et al., Effect of anions on model aluminum-containing vaccines, J Colloid & Interface Science 172: 121-130 (1995).
Gupta, et al., Biodegradable Polymer Microspheres as Vaccine Adjuvants and Delivery Systems, Dev Biol Stand, vol. 92: 63-78 (1998).
Payne, et al., PCPP as a parental adjuvant for diverse antigens, Dev Biol Stand, vol. 92: 79-87 (1998).
Constancis, et al., Macromolecular colloids of diblock poly(amino acids) that bind insulin, J Colloid & Interface Science 217: 357-368 (1999).
Gupta, et al., Evaluation of a Guinea Pig Model to Assess Interference in the Immunogenicity of Different Components of a Combination Vaccine Comprising Diphtheria, Tetanus and Acellular Pertussis (DTaP) Vaccine and *Haemophilus influenzae* type b Capsular Polysaccharide Conjugate Vaccine, Biologicals, vol. 27: 167-176 (1999).
Sanchez, et al., Formulation strategies for the stabilization of tetanus toxoid in poly(lactide-co-glycolide) microspheres. Int J Pharmaceutics, vol. 185: 255-266 (1999).
Jiang and Schwendeman, Stabilization of a Model Formalinized Protein Antigen Encapsulated in Poly(lactide-co-glycolide)-Based Microspheres. J Pharmaceutical Sciences, vol. 90(10): 1558-1569 (2001).
Von Hunolstein, et al., The adjuvant effect of synthetic oligodeoxynucleotide containing CpG motif converts the anti-*Haemophilus influenzae* type b glycoconjugates into efficient anti-polysaccharide and anti-carrier polyvalent vaccines. Vaccine, vol. 19: 3058-3066 (2001).

(Continued)

*Primary Examiner* — Jennifer Graser
(74) *Attorney, Agent, or Firm* — Alice P. Bradney

(57) ABSTRACT

The present invention relates to methods of reducing flocculation in an immunogenic composition, where said immunogenic composition comprises (a) *Haemophilus influenzae* B capsular polysaccharide or oligosaccharide (PRP) and (b) at least one non-PRP antigen. The invention further relates to kits comprising (i) a first composition comprising a *Haemophilus influenzae* B capsular polysaccharide or oligosaccharide (PRP) and a polyanionic polymer, and (ii) a second composition comprising a non-PRP antigen adsorbed onto an adjuvant with a zero point charge greater than 8.

30 Claims, 6 Drawing Sheets

(56) References Cited

OTHER PUBLICATIONS

Boehm, et al., On Technological and Immunological Benefits of Multivalent Single-Injection Microsphere Vaccines. Pharmaceutical Research. vol. 19(9): 1330-1336 (2002).

Diwan, et al. Enhancement of immune responses by co-delivery of a CpG oligodeoxynucleotide and tetanus toxoid in biodegradable nanospheres. J Controlled Release, vol. 85: 247-262 (2002).

Glaxosmithkline NZ Ltd, Datasheet—Hiberix, New Zealand Medicines and Medical Devices Safety Authority (2002).

Nicol, et al., Poly-L-glutamate, an anionic polymer, enhances transgene expression for plasmids delivered by intramuscular injection with in vivo electroporation. Gene Therapy, vol. 9(20): 1351-1358 (2002).

Raghuvanshi, et al., Improved immune response from biodegradable polymer particles entrapping tetanus toxoid by use of different immunization protocol and adjuvants. Int J Pharmaceutics, vol. 245: 109-121 (2002).

Richard and Margaritis, Production and Mass Transfer Characteristics of Non-Newtonian Biopolymers for Biomedical Applications. Critical Reviews in Biotechnology, vol. 22(4): 355-374 (2002).

Yang, et al., Poly(glutamic acid) poly(ethylene glycol) hydrogels prepared by photoinduced polymerization: synthesis, characterization, and preliminary release studies of protein drugs. J Biomed Mater Res, vol. 62(1): 14-21 (2002).

Milas, et al., Poly(L-glutamic acid)-Paclitaxel Conjugate is a Potent Enhancer of Tumor Radiocurability, Int J Radiation Oncology Biol Phys, vol. 55(3): 707-712 (2003).

Peyre, et al., An Experimental Divalent Vaccine Based on Biodegradable Microspheres Induces Protective Immunity Against Tetanus and Diphtheria. J Pharm Sci, vol. 92(5): 957-966 (2003).

Aldrich Handbook of Fine Chemicals and Laboratory Equipment, 2003-2004, United Kingdom, pp. 1529-1530.

Lactel® Absorbable Polymers MSDS for 50:50 poly(DL-lactide-co-glycolide), Apr. 8, 2008, from Birmingham Polymers, www.birminghampolymers.com, www.absorbables.com/documents/DL-PLGMSDS.pdf.

Figure 1: *Pre-saturation of Al(OH)$_3$ with PLG (106 residues)*
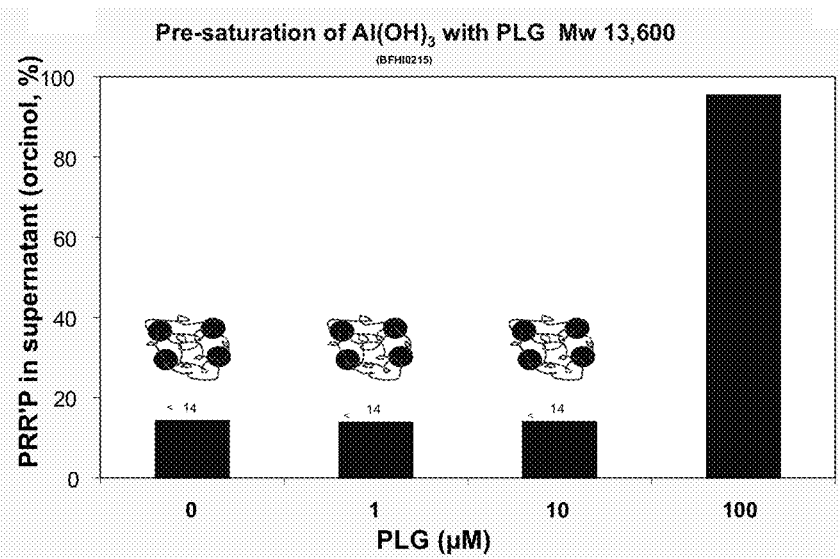
Figure 2: *Competition between PRP-T and PLG (85 residues)*
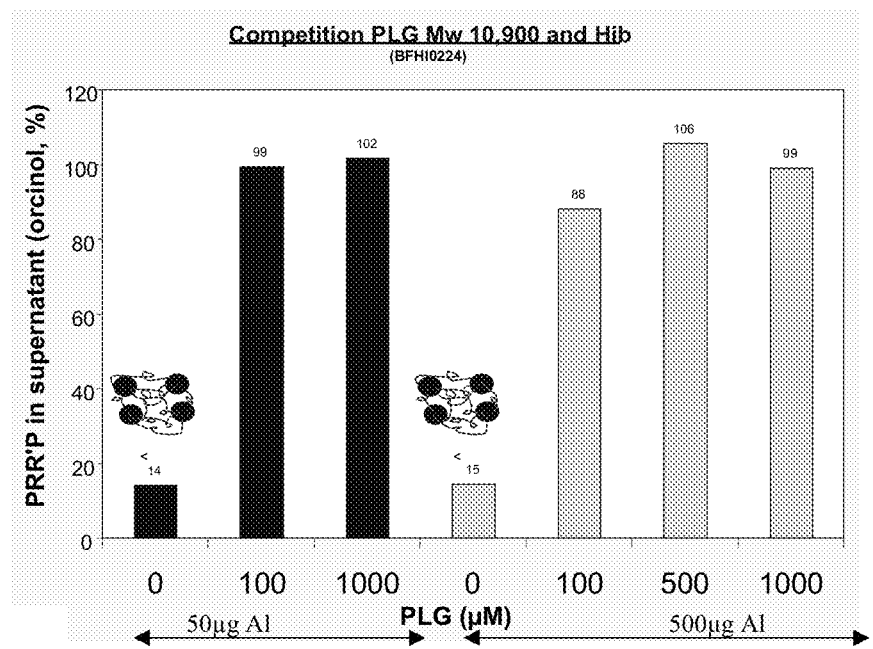

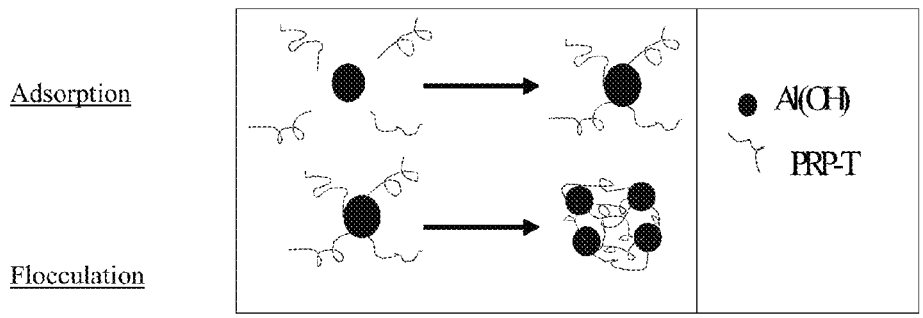
Figure 5: *Schematic representation of adsorption and flocculation.*
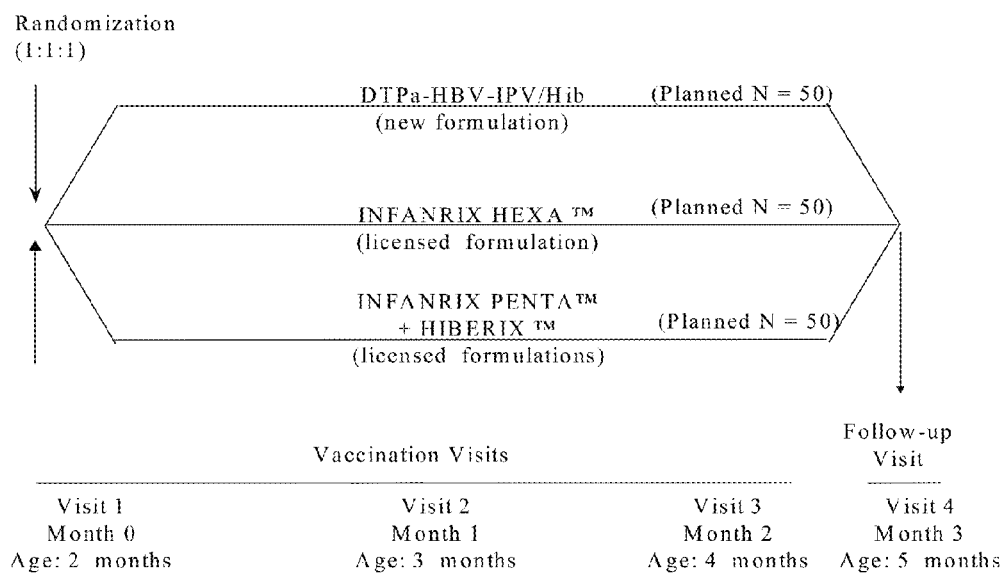
Figure 6: *Scheme of clinical trial*

POLYANIONIC POLYMER ADJUVANTS FOR HAEMOPHILUS INFLUENZAE B SACCHARIDE VACCINES

This application is a continuation of U.S. application Ser. No. 13/919,024 filed Jun. 17, 2013, now pending, which is a continuation of U.S. application Ser. No. 13/396,843, filed Feb. 15, 2012, now abandoned, which is a continuation of U.S. application Ser. No. 12/785,809, filed May 24, 2010, now U.S. Pat. No. 8,137,681, issued Mar. 20, 2012, which is a continuation of U.S. application Ser. No. 10/560,513, filed Dec. 13, 2005, now U.S. Pat. No. 8,007,818, issued Aug. 30, 2011, which was the U.S. National Stage Application of International Application No. PCT/EP2004/006426, filed Jun. 14, 2004, which claims priority to United Kingdom Application No. GB 0313916.9, filed Jun. 16, 2003, the entire contents of which are incorporated herein.

The present invention relates to the field of vaccines, and, in particular, to immunogenic compositions comprising antigens of low isoelectric point such as *H. influenzae* B capsular polysaccharide or oligosaccharide (PRP). The present invention presents immunogenic compositions and combination vaccines comprising PRP wherein the PRP is protected to some degree from immune interference that can occur when PRP is combined with other antigen formulations—particularly formulations comprising DTPa; a well known 'trivalent' combination vaccine comprising Diphtheria toxoid (DT), tetanus toxoid (TT), and acellular *B. pertussis* components [typically comprising detoxified pertussis toxoid (PT) and filamentous hemagglutinin (FHA) with optional pertactin (PRN) and/or agglutinogens 2 and 3], typically adsorbed (at least in part) on aluminium hydroxide adjuvant, for example the marketed vaccine INFANRIX-DTPa™ (GlaxoSmithKline Biologicals) which contains DT, TT, PT, FHA, and PRN antigens, all adsorbed onto aluminium hydroxide adjuvant. A method to reduce interference of PRP in a combination vaccine (comprising, for instance, DTPa) is also presented.

Vaccines that utilise polysaccharides are known in the art. For example a PRP vaccine for the prevention of *Haemophilus influenzae* B infections is based on the *H. influenzae* B capsular oligosaccharide or polysaccharide (PRP) conjugated with a carrier protein. The polysaccharide is a polymer of ribose, ribitol and phosphate. Examples of carrier protein include diphtheria or tetanus toxoid, or an outer membrane protein of *N. meningitidis*. See for example U.S. Pat. No. 4,365,170, U.S. Pat. No. 4,673,574, EP 208375, EP 477508 and EP 161188.

It is desirable to administer such conjugate vaccines with other antigens or vaccines at the same time and this can involve multiple injections. Problems associated with multiple injections include a more complicated administration procedure and a large total injection volume. This is a particularly acute problem when the vaccine is intended for infants. For both the infant and the practitioner it is desirable to inject all necessary antigens in one shot of normal volume, thus rendering the vaccination procedure less traumatic and painful for the infant, and more efficient and easier to manage for the practitioner.

It has therefore been proposed to combine such polysaccharide conjugate vaccines with other vaccines such as DTPa or DTPw (where the pertussis component is killed whole-cell *Bordetella pertussis*) to produce more elaborate combination vaccines. In addition, the inclusion of further antigens to such a combination vaccine for the prevention of diseases like hepatitis B or Polio has also been proposed (combination vaccines comprising an antigen against hepatitis B and antigens against diphtheria, tetanus and pertussis (HepB, DTPa) have been described in WO 93/24148). See also WO 98/00167 and WO 99/13906 which also disclose DTP-PRP combination vaccines.

It has been found, however, that simple mixing of the components of a combination vaccine is complicated by the fact that not all antigens can be effectively mixed together. The reduction in the immunogenicity of an antigen when combined with other components (as compared to the particular antigen administered alone) is known as interference. It is known, for example, that the extemporaneous mixing of a DTPa combination vaccine with unadjuvanted PRP conjugates results in a reduction of antibody titres to the PRP polysaccharide (WO 97/00697). In addition, WO 97/00697 showed that if PRP conjugate is adsorbed onto aluminium hydroxide, there is a significant reduction of antibody titres to the polysaccharide component. These results indicated that there was interference between the aluminium hydroxide of the DTPa vaccine and PRP. In order to try and minimise this interference in such an extemporaneously-prepared combination vaccine PRP was pre-adsorbed onto aluminium phosphate.

Without wishing to be bound by theory, it is thought that the above interference problem may be as a result of PRP (with a low isoelectric point of less than 2) forming a strong interaction with aluminium hydroxide (with a high isoelectric point). This interaction may mask PRP epitopes from immune competent cells—particularly if the PRP/AlOH interaction forms a network of particles—a phenomenon called flocculation (see FIG. 5) which may be observed visually or by optical microscope.

WO 96/37222 also describes the interference problem. In this case the antigenicity of PRP conjugate is stabilised by adsorbing it and the other DTPa components onto an aluminium-based adjuvant with a zero point charge (ZPC) of less than 7.2, for instance aluminium phosphate, or aluminium hydroxide to which anion salts have been added to lower its zero point charge from around 10 or 11 to under 7.2.

A problem with using aluminium phosphate entirely for a combination vaccine is that many antigens in a combination vaccine benefit immunologically from being adsorbed onto aluminium hydroxide—for instance pertactin. Many of these antigens (for instance pertactin) cannot be adequately adsorbed onto aluminium phosphate, and become desorbed from aluminium hydroxide if sufficient anion salts are added to reduce its zero point charge under 7.2. Pertactin is one of the most important components in the pertussis vaccine. Without wishing to be bound by theory, a significant lowering of its adsorption on adjuvant could lead to a reduction of the T-cell response and the potency of the acellular pertussis vaccine as a whole. At pH 6.1 (the typical pH of DTPa vaccines) a 24 hour adsorption step allows more than 90% of pertactin to be adsorbed onto aluminium hydroxide, but less than 50% to be adsorbed onto aluminium phosphate (reducing further when it is combined with other antigens).

There is therefore a technical problem in combination vaccines comprising PRP and antigens adsorbed onto aluminium hydroxide to reduce interference to PRP, yet maintain a significant degree of adsorption of antigens beneficially associated with aluminium hydroxide. A further technical problem is that antigens of low pI can form aggregates (or flocculate) with adjuvant particles making the vaccine unsuitable for use.

WO 99/48525 provides one solution to this problem which involves a complex process of adsorbing and mixing antigens in order for PRP to be added with minimised interference.

There is still need, however, for further solutions to the above problems which are advantageously simpler—i.e.

involve a single, simple additional process step, or involve the simple addition of a single PRP-protective excipient to the immunogenic composition. The present invention provides such a solution.

BRIEF DESCRIPTION OF THE DRAWINGS

FIG. 1: Pre-saturation of Al(OH)$_3$ with PLG (106 residues).

FIG. 2: Competition between PRP-T and PLG (85 residues).

FIG. 5: Schematic representation of adsorption and flocculation.

FIG. 6: Scheme of clinical trial.

DESCRIPTION OF THE INVENTION

This invention relates to a general method by which either extemporaneously-prepared or liquid PRP/DTPa combination vaccines (or PRP/DTPw) can be made in order to reduce the PRP interference problem whilst being able to maintain a significant degree of adsorption of antigens beneficially associated with the aluminium-based adjuvant on which it is most immunogenic. In so doing, pertussis antigens in combination vaccines of the present invention may be stably retained in their most potent form. The invention further provides immunogenic compositions, vaccines and combination vaccines comprising PRP which is protected to some degree from immune interference. The inventors have found that the above can surprisingly be achieved by incorporating a polyanionic polymer excipient with the vaccine comprising PRP. Without wishing to be bound by theory, the polyanionic polymer can compete with PRP, protecting it from any aluminium hydroxide present in the vaccine (for example by reducing the amount or rate of binding of PRP to adjuvant and/or the extent or rate of flocculation), yet surprisingly does not cause antigens already adsorbed to aluminium hydroxide to become significantly desorbed.

Accordingly in one embodiment the present invention provides an immunogenic composition comprising a capsular polysaccharide or oligosaccharide of *Haemophilus influenzae* B (PRP), and a polyanionic polymer.

Although PRP is described throughout this specification, it is envisaged that the same solution may protect other oligosaccharides or polysaccharides (or antigens in general) with a low isoelectric point (less than 4 or less than 3, preferably less than 2), and therefore wherever PRP is mentioned herein, such other oligosaccharides, polysaccharides or antigens may alternatively be included as part of the invention. The isoelectric point (pI) above is that of the saccharide moiety before any conjugation event. In particular capsular polysaccharide or oligosaccharide isolated from *N. meningitidis* serogroup A or C may alternatively be used, the polyanionic polymer also functioning to prevent, for instance, potential aggregation and/or immunogenicity reduction events in the vaccines (for instance based on DTPa or DTPw combinations) of the invention (see Example 2). Thus an immunogenic composition comprising an antigen (preferably saccharide) with a low pI and a polyanionic polymer is envisioned.

By "oligosaccharide" and "polysaccharide" it is meant a saccharide epitope that has been isolated from a pathogen (for instance from a bacterial cell's capsular polysaccharide). It may be isolated directly from the bacterium, or may be processed in some way before use in the vaccines of the invention; for instance it may have been reduced in size by known techniques such as microfluidisation (see EP 497524 for other such size reduction techniques). The term "polysaccharide or oligosaccharide" throughout this specification may therefore be replaced by the term "saccharide".

Figure 7:
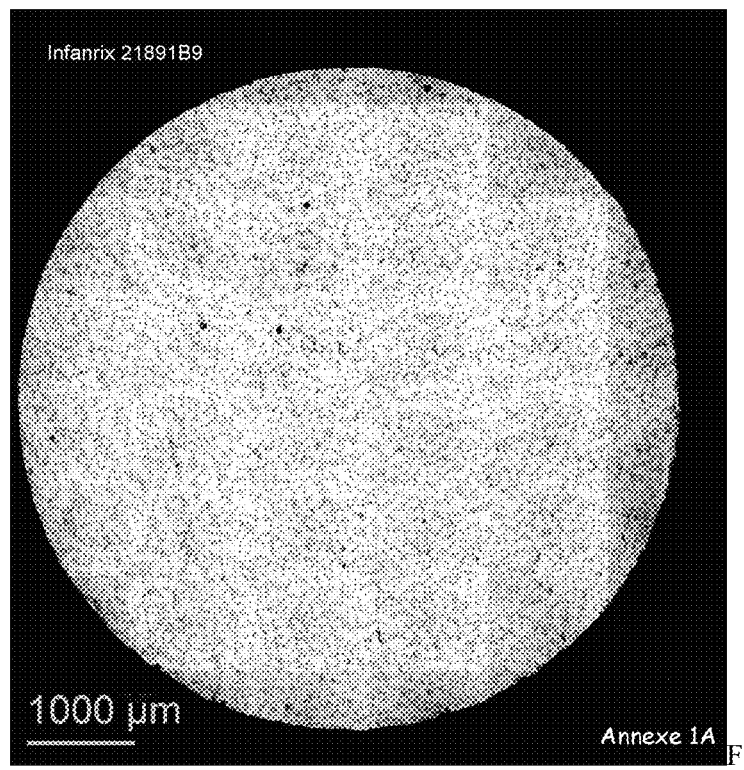
FIG. 7: Optical microscope picture of INFANRIX PENTA™ (DTPaHepBIPV).
Figure 8:
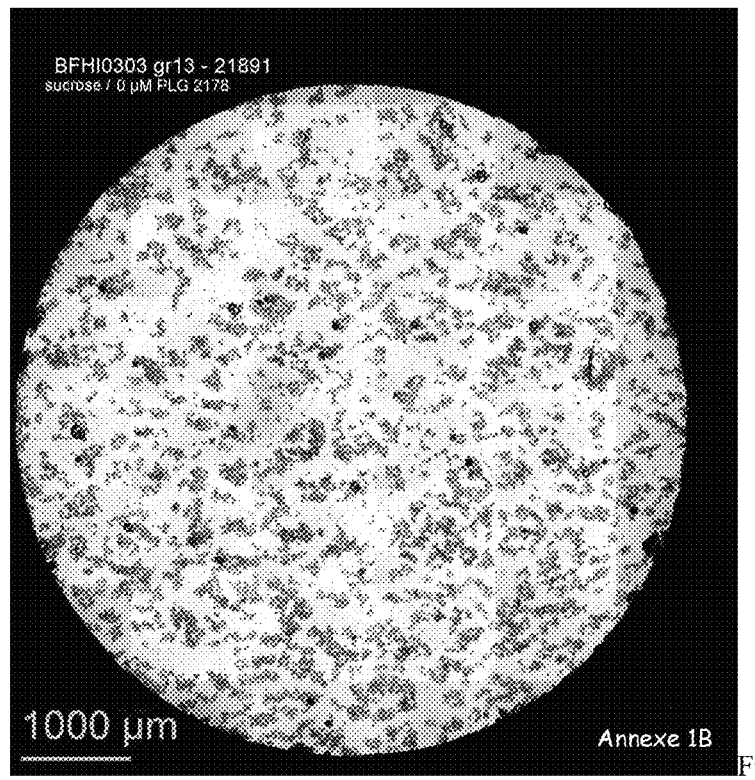
FIG. 8: Optical microscope picture of sample flocculating when 5 μg saccharide of PRP-TT is added to the sample.
Figure 11:
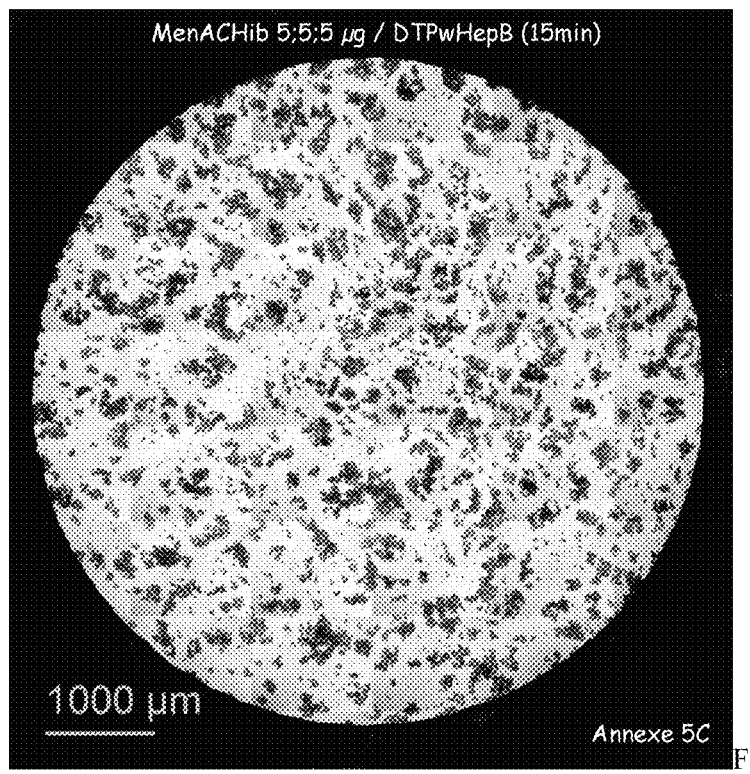
FIG. 11: Optical microscope picture showing observable flocculations in DTPw samples with reconstituted MenACHib-TT.

By "protection" of an antigen with low pI from adjuvants with high pI (such as AlOH) it is meant any or all of the following: a) that the antigen exhibits reduced binding to the adjuvant if the polyanionic polymer is present, and/or b) that flocculation between antigen and adjuvant is reduced (preferably prevented) if the polyanionic polymer is present (for instance assessed by using optical microscopy techniques in Example 2, FIGS. 8 and 11 showing flocculated samples, and FIGS. 7, 9, 10, 12 showing non-flocculated samples), and/or c) immune interference to the antigen is reduced (and preferably prevented) if the polyanionic polymer is present (as measured by ELISA tests to establish GMT or GMC of anti-antigen antibody in sera of immunised animals).

The terms "comprising", "comprise" and "comprises" herein is intended by the inventors to be substitutable with the terms "consisting of", "consist of" and "consists of", respectively, in every instance.

In a preferred embodiment, PRP (or antigen of low pI) is conjugated to a carrier protein which is a source of T-helper cell epitopes.

Preferred carrier proteins for the polysaccharide or oligosaccharide conjugates of the present invention are tetanus toxoid, diphtheria toxoid, CRM197, an outer membrane protein from a bacteria such as *N. meningitidis*, and protein D from non-typeable *H. influenzae* (EP594610). Most preferably, PRP (or other saccharide antigens of low pI) is conjugated to tetanus toxoid. The synthesis of *Haemophilus influenzae* type B capsular polysaccharide (PRP) tetanus toxoid (TT) conjugate is described, for example, in WO 97/00697.

The polysaccharide or oligosaccharide conjugates of the invention may be prepared by any known coupling technique. For example the polysaccharide can be coupled via a thioether linkage. This conjugation method relies on activation of the polysaccharide with 1-cyano-4-dimethylamino pyridinium tetrafluoroborate (CDAP) to form a cyanate ester. The activated polysaccharide may thus be coupled directly or via a spacer group to an amino group on the carrier protein. Preferably, the cyanate ester is coupled with hexane diamine and the amino-derivatised polysaccharide is conjugated to the carrier protein using heteroligation chemistry involving the formation of the thioether linkage. Such conjugates are described in PCT published application WO93/15760 (Uniformed Services University).

The conjugates can also be prepared by direct reductive amination methods as described in U.S. Pat. No. 4,365,170

(Jennings) and U.S. Pat. No. 4,673,574 (Anderson). Other methods are described in EP 161188, EP 208375 and EP 477508.

A further method involves the coupling of a cyanogen bromide activated polysaccharide derivatised with adipic acid hydrazide (ADH) to the protein carrier by carbodiimide condensation. Such conjugation is described in Chu C. et al. Infec. Immunity, 1983 245 256.

A polyanionic polymer of the present invention is a polymer which, when dissolved in an aqueous medium at pH7 (and preferably also at pH 6.1—a typical pH of the DTPa and DTPw vaccines of the invention), is negatively-charged due to the presence of anionic constitutional repeating units (for example, units containing sulphate, sulphonate, carboxylate, phosphate and borate groups). A constitutional repeating unit or monomer refers to the minimal structural unit of a polymer. The polyanionic polymer may be a polyanionic heteropolymer, comprising two or more different anionic constitutional repeating units, or may be a polyanionic homopolymer, consisting of a single anionic constitutional repeating unit. Although preferred, clearly not every monomer/repeat unit need be negatively charged as long as there is sufficient negative charge for the polyanionic polymer of the invention to have the capabilities stated herein, in particular the ability to prevent flocculation between PRP and aluminium hydroxide adjuvant and/or the capability not to significantly desorb antigens beneficially adsorbed to aluminium hydroxide.

The polyanionic polymer of the invention may be a chemical polymer and may comprise anionic constitutional repeating units obtained from a group consisting of: acrylic acid, methacrylic acid, maleic acid, fumaric acid, ethylsulphonic acid, vinylsulphonic acid, vinylsulphonic acid, styrenesulphonic acid, vinylphenylsulphuric acid, 2-methacryloyloxyethane sulphonic acid, 3-methacryloyloxy-2-hydroxypropanesulphonic acid, 3-methacryl amido-3-methylbutanoic acid, acrylamidomethylpropanesulfonic acid, vinylphosphoric acid, 4-vinylbenzoic acid, 3-vinyl oxypropane-1-sulphonic acid, N-vinylsuccinimidic acid, and salts of the foregoing.

Alternatively, the polyanionic polymer of the invention may (or may not, as this is not a preferred embodiment) be an oligo- or poly-saccharide such as dextran.

Most preferably, the polyanionic polymer of the invention is an oligo- or poly-peptide. Such peptides may be D- or L-peptides (preferably the latter so that peptide is advantageously bio-degradable), and may comprise anionic constitutional repeating units (or monomers) such as L-aspartic acid, D-aspartic acid, L-glutamic acid, D-glutamic acid, non-natural anionic amino acids (or salts or anionic chemical derivatives thereof).

For the purposes of this invention, the polyanionic polymer of the present invention is an oligo- or poly-peptide which has a monomer content of no less than 30, 40, 50, 60, 70, 80, 90 or, preferably, 100% L-aspartic acid and/or L-glutamic acid.

Preferably the polyanionic polymer of the invention consists of, on average, 4-200 or 5-200 monomers, preferably 8-117 monomers, more preferably 15-32 or 15-18 monomers, most preferably 17 monomers (or residues in the case of peptides). As polymers are complex populations of molecules of potentially different lengths, "on average" means that number of monomers or residues is calculated according to the weight-average molecular weight (or $M_w$) of the polyanionic polymer measured by MALLS divided by the molecular weight of the monomer. Preferably the polydispersity (a measure of homogeneity) of the polyanionic polymer is less than 3. Multiple angle laser light scattering (MALLS) is a well known technique for obtaining $M_w$ and polydispersity measurements of polymers (and is typically carried out using a TSKG3000PWXL HPLC column at flow rate 0.75 ml/min, eluted in 10 mM phosphate buffer pH 7.6, 130 mM NaCl). It is also envisaged that the polyanionic polymer of the invention may comprise mixtures of 2 or more polyanionic polymers with different $M_w$s. For instance blends of 16mers and 8mers or 16mers and 4mers of the same type of polymer may be advantageously used for the purposes of this invention.

Without wishing to be bound by theory, it is thought that polyanionic polymers have advantages over using anions or anionic monomers, as anions have to be present at a high concentration in a vaccine to prevent PRP binding and/or flocculating with AlOH adjuvant. At such high concentrations antigens beneficially adsorbed onto the adjuvant becomes desorbed. Polyanionic polymers are thought to have the twin properties of low pI, and high binding affinity for AlOH that allows smaller concentrations of the excipient to be used sufficient to prevent the PRP interference/flocculation problem but insufficient to cause significant or excessive desorption of antigens beneficially adsorbed onto AlOH.

In a particularly preferred embodiment the polyanionic polymer of the invention is a poly-L-glutamic acid (PLG) homopolymer. Low molecular weight PLG (less than 6000 $M_w$, preferably 640-5000) is particularly preferred (for instance PLG with on average 17 residues with a $M_w$ of 2178) for optimal clearance from the body post-administration and to ensure it does not induce an immune response itself in the host.

PLG is a fully bio-degradable polyamino acid with a pendent free γ-carboxyl group in each repeat unit (pKa 4.1) and is negatively charged at a pH7, which renders this homopolymer water-soluble and gives it a polyanionic structure. PLG may be made using conventional peptide synthesis techniques. It is also available from Sigma-Aldrich in a relatively polydisperse form (e.g. 17mers with a polydispersity around 2.6), or from Neosystem in a relatively monodisperse form (e.g. 8, 16, 24 or 32mers with a polydispersity close to 1). For a preferred 17mer of the invention (e.g. from Sigma), PLG is typically present at a concentration of 290 µg/ml. For a preferred 16mer of the invention (e.g. from Neosystems), PLG is typically present at a concentration of 125-600 µg/mL, preferably around 300 or 400 µg/ml, although the skilled person will appreciate that the above quantities may vary to some degree depending on the precise composition of the vaccine.

α-PLG is currently used for two main biomedical applications: drug delivery for cancer therapy (Li et al., Clin. Cancer. Res. 6:2829-2834, 2000) and biological glue (Iwata et al., Biomaterials 19:1869-1876, 1998). It has not been used as an excipient for intramuscular vaccination.

There are several variables that exist in a vaccine sample which allow the skilled person to determine the appropriate quantity of polyanionic polymer (or blend of polyanionic polymers of different $M_w$s) that should be used in a vaccine. In general only just enough polyanionic polymer should be used such that flocculation and/or PRP immune interference is prevented. Often the polyanionic polymer is present at a higher concentration in the vaccine than that of the PRP saccharide. Factors to consider when determining the amount of polyanionic polymer to use are:

1) Charge of the polyanionic polymer—as it becomes more negative, less concentration required in the sample. 2) Size of polyanionic polymer chain (on average)—as it increases, less concentration required in the sample. 3) Polydispersity of polyanionic polymer—higher quantities may be required if uneven bias to low molecular weight species in the sample. 4) Amount of PRP (or saccharide antigen of low pI)—this may be from 1-20 µg/dose/PS—as amount increases, more polyanionic polymer may be required. 5) Size of the PRP (or saccharide antigen of low pI)— as the size increases from oligosaccharide to polysaccharide so may binding affinity to AlOH adjuvant (for instance), thereby requiring more polyanionic polymer. 5) Ratio of PRP(saccharide):carrier (5:1 to 1:5 w/w)—as steric hindrance in the conjugate increases polyanionic polymer quantities may need to be adjusted. 6) Charge of adjuvant (with a ZPC >8)—as charge increases at same pH, more polyanionic polymer should be required. 7) Size of adjuvant (e.g. AlOH) particle—although it should always be of an injectable size—for a given amount of adjuvant, if increased size less polyanionic polymer should be required. 8) Amount of adjuvant (acceptable range for vaccines being 50-1250 µg per dose $Al^{3+}$)—as amount increases, more polyanionic polymer may be required. 9) Presence of other adsorbed antigens—as a greater amount of Ag is adsorbed on surface of the adjuvant, less polyanionic polymer should be required.

An assessment of flocculation may be readily carried out be techniques known in the art such as sedimentation profile, optical microscopic (Example 2), or even visual observation. In general, vaccines of the invention comprising adjuvant with a ZPC >8 should be less aggregated (preferably no flocculation observed) than the equivalent formulation without polyanionic polymer after 15 minutes of mixing the PRP saccharide with the vaccine. The conservation of anti-PRP antibody titres (or reduction of interference to the development of such titres) may be assessed by standard ELISA tests.

Particularly preferred immunogenic compositions of the invention comprise PRP (preferably conjugated) and polyanionic polymer that are advantageously formulated such that the result of multiplying the concentration of the polyanionic polymer in the composition (in µM) by the net negative charge of the polyanionic polymer at pH 7.0 divided by the amount of PRP present in a 0.5 mL dose of the immunogenic composition (in µg) is 300-6000, preferably 400-4000, more preferably 500-2000, 560-1100, 610-900, 640-800, or 660-700, and most preferably around or exactly 680. The concentration of the polyanionic polymer in the composition should again be measured according to the $M_w$ of polyanionic polymer used, and is typically in the range 30-2000 µM, preferably 80-1000, 100-500, 150-300, and most preferably around or exactly 200 µM. Alternatively concentration may be expressed in units of µ/ml, being typically in the range 45-3000 µg/ml, preferably 120-1500, 150-750, 225-450, and most preferably around or exactly 290 or 300 µg/ml.

The net negative charge at pH7.0 of the polyanionic polymer may be calculated by any suitable means. Again this may be an average property of the polymer, and should be calculated with respect to the $M_w$ of polyanionic polymer used. For instance, a PLG polymer with on average 17 residues should have a net negative charge of 17. Preferably the net negative charge should be at least 8, or at least 17, preferably 8-106, 10-80, 12-60, 14-40, 16-20, and most preferably around or exactly 17.

It is preferred that the polyanionic polymer of the invention has at least on average 1 net negative charge at pH 7.0 per 3 monomers, preferably at least 2 per 3 monomers, and most preferably at least on average 1 net negative charge for each monomer. The charges may be unevenly arranged over the polymer length, but are preferably evenly spread over the polymer length.

The immunogenic compositions of the invention typically comprise 1-20, preferably 2.5-10, and most preferably around or exactly 5 µg of PRP (preferably conjugated to carrier protein, the weight of which is not counted in the above calculations) per 0.5 mL dose. PRP is most preferably not intentionally adsorbed onto any adjuvant.

In a highly preferred embodiment an immunogenic composition is provided comprising 5 µg of PRP conjugated to a carrier protein (preferably tetanus toxoid) and 218 µg of poly-α-L-glutamic acid sodium (approximately 200 µM) per 0.5 mL human dose, wherein the PLG contains on average 17 glutamic acid residues (preferably with a $M_w$ 2,178, and optionally with a polydispersity of 2.6).

In all the above immunogenic compositions, further excipients may be added to those already mentioned. In particular, PRP may be adsorbed onto aluminium phosphate adjuvant (as described in WO 97/00697 and WO 99/48525) but is preferably unadsorbed. The immunogenic composition may be buffered with any suitable buffer that has a pKa that may stabilise the pH of the composition—typically pH6-7, most preferably pH 6.1. For example Histidine buffer may be used, or, preferably, maleate buffer. In general, buffers (and quantities used) should be selected that do not significantly effect the polyanionic polymer's beneficial effect in the composition. In general if a buffer is present, less than 10, 5, 4, 3, 2, 1, 0.5 or 0.1 mM buffer should be used, preferably around 2 mM.

If the immunogenic composition of the invention is to be lyophilised for storage purposes, it is preferable that a stabilizing excipient (or cryoprotector) is added to the composition. Any such excipient may be used such as glucose, maltulose, iso-maltulose, lactulose, sucrose, sorbitol, maltose, lactose, iso-maltose, maltitol, lactitol, palatinit, trehalose, raffinose, stachyose, and melezitose, but preferably sucrose is used. Such excipients are typically present in the amount of 1-5%, and preferably around or exactly 2.5% (w/v).

Although the immunogenic compositions of the invention may have an antigenic content consisting of only PRP (preferably conjugated to a protein carrier), it may comprise one or more further antigens. PRP may be mixed and stored with these other antigens, or may have them added extemporaneously (by a practitioner just before administering the composition to a patient in need thereof). The polyanionic polymer may be added to the one or more other antigens before PRP is combined with them, or, preferably is present with the PRP as a protectant before the other antigens are combined with it. Some of the further antigens may be stored with PRP (preferably lyophilised) and some stored separately (preferably liquid) to be reconstituted together extemporaneously, wherein the polyanionic polymer may be present in either composition, but is preferably present with the PRP.

Preferably, the immunogenic composition in addition to PRP (preferably conjugated) and polyanionic polymer further comprises one or more meningococcal capsular oligosaccharide or, preferably, polysaccharide—carrier protein conjugates (see above for preferred carrier proteins comprising T-helper epitopes, most preferably tetanus toxoid) selected from a group consisting of: MenC, MenY, MenA and MenW (e.g. A+C, A+Y, A+W, C+Y, C+W, Y+W, A+C+Y, A+C+W, A+Y+W, C+Y+W, A+C+Y+W); preferably MenC and/or MenY is included, and most preferably all 4. These meningococcal components are preferably not intentionally adsorbed onto any adjuvant. Such immunogenic compositions are beneficially lyophilised, and may be reconstituted with further antigens (for instance DTPa- or DTPw-based compositions), preferably extemporaneously. By "extemporaneously" herein it is meant that the vaccine is administered within 1.5 hours or 1 hour of making up the combined vaccine, preferably within 0.5 hour, most preferably within 15 minutes.

Alternatively or in addition to the above meningococcal antigens, the immunogenic composition may comprise one or more pneumococcal capsular oligosaccharide or polysaccharide—carrier protein conjugates (see above for preferred carrier proteins comprising T-helper epitopes, most preferably CRM197, diphtheria toxoid, tetanus toxoid or protein D).

Typically pneumococcal capsular oligosaccharides or polysaccharides (preferably the latter) represented in the compositions of the invention comprise antigens derived from at least four serotypes of pneumococcus. Preferably the four serotypes comprise 6B, 14, 19F and 23F. More preferably, at least 7 serotypes are comprised in the composition, for example those derived from serotypes 4, 6B, 9V, 14, 18C, 19F, and 23F. More preferably still, at least 11 serotypes are comprised in the composition (11 valent), for example those derived from serotypes 1, 3, 4, 5, 6B, 7F, 9V, 14, 18C, 19F and 23F. In a preferred embodiment of the invention at least 13 of such conjugated pneumococcal antigens are comprised, although further antigens, for example 23 valent (such as serotypes 1, 2, 3, 4, 5, 6B, 7F, 8, 9N, 9V, 10A, 11A, 12F, 14, 15B, 17F, 18C, 19A, 19F, 20, 22F, 23F and 33F), are also contemplated by the invention.

For elderly vaccination (for instance for the prevention of pneumonia) it is advantageous to include serotypes 8 and 12F (and most preferably 15 and 22 as well) to the 11 valent pneumococcal antigenic composition described above to form a 15 valent composition, whereas for infants or toddlers (where otitis media is of more concern) serotypes 6A and 19A are advantageously comprised to form a 13 valent composition.

Again such immunogenic compositions comprising pneumococcal antigens are beneficially lyophilised, and may be reconstituted with further antigens (for instance DTPa-based compositions), preferably extemporaneously.

The immunogenic composition of the invention in addition to PRP and polyanionic polymer may further comprise one or more (2 or preferably all 3 [a DTPw or DTPa composition]) further antigens or antigen groups selected from tetanus toxoid (TT), diphtheria toxoid (DT), and whole-cell or one or more acellular *B. pertussis* antigens. The one or more (2, 3, 4 or all 5) acellular *B. pertussis* antigens that may be comprised may be selected from the group consisting of: pertussis toxoid (PT), FHA, pertactin (PRN), agglutinogen 2 and agglutinogen 3 (and preferably comprises the first three).

Such DTPa or DTPw compositions may further comprise either or both of Inactivated Polio Vaccine (IPV) (typically unadsorbed before mixing) and Hepatitis B surface antigen (which is preferably adsorbed onto aluminium phosphate as described in WO 93/24148).

DT, TT, PT, FHA and PRN are well known in the art. The PT component may be made into a toxoid either chemically or genetically, for example as described in EP 515415. See also EP 427462 and WO 91/12020 for the preparation of pertussis antigens. Optionally the PT component may be recombinant (for example as described in European Patent Applications EP 306318, EP 322533, EP 396964, EP 322115 and EP 275689). Optionally the DT and TT components may also be recombinant. Typically the PT, FHA, PRN, HBsAg (Hepatitis B surface antigen), and PRP components will be in the range 8-25 µg per 0.5 mL dose of bulk vaccine. The DT, TT, and IPV (inactivated trivalent poliovirus vaccine) components should typically be present as approximately 15-25 Lf (flocculating units), 10 Lf, and 40/8/32 (type I/II/III) DU respectively per 0.5 mL dose of bulk vaccine.

Suitable components for use in such vaccines are already commercially available and details may be obtained from the World Health Organisation. For example the IPV component may be the Salk inactivated polio vaccine. The Hepatitis B surface antigen may comprise the 'S' antigen as in ENGERIX-B® (SmithKline Beecham Biologicals).

The addition of either lyophilised or liquid PRP (either unadjuvanted or adsorbed onto aluminium phosphate) to a solution of the other components of the composition may be performed extemporaneously (see above), or before the vaccine leaves the manufacturer. PRP may be combined with polyanionic polymer before its addition to the other components, or PRP may be added to other components further comprising polyanionic polymer.

The immunogenic compositions of the invention will typically further comprise an adjuvant with a zero point charge greater than 8, 9 or 10, typically an aluminium salt, most often alum or aluminium hydroxide. This will particularly be the case for DTPa-containing compositions where one or more DTPa component is preferentially adsorbed onto aluminium hydroxide. Usually such adjuvant is present in the immunogenic composition in the amount of 50-1250 or 100-1000 µg per 0.5 mL dose, usually around or exactly 500 µg per 0.5 mL dose, of which around 50, 60, 70, 80, 90 or 95% has antigen (non-PRP, usually one or more DTPa antigens) specifically adsorbed onto its surface.

The presence of such adjuvants would normally tend to flocculate with any PRP present in the composition, however in the immunogenic compositions of the present invention this is prevented by the presence of the polyanionic polymer.

Alternatively, and preferably additionally, the presence of the polyanionic polymer can reduce the immunological interference that the adjuvant has on PRP by over 20, 30, 40, 50, 60, 70, 80, 90, or, preferably, by 100% (interference being measured by taking the difference in anti-PRP GMT titres in (µg/mL) in an appropriate model [e.g. mouse or rat, or in a well-conducted human clinical trial] between administering a PRP vaccine by itself versus the same PRP vaccine in an immunogenic composition comprising the above adjuvant; the reduction of interference being the extent to which the GMT in the immunogenic composition is restored to that of the PRP vaccine by itself by the addition of the polyanionic polymer of the invention to the immunogenic composition).

Where the above adjuvant (with a zero-point charge greater than 8, 9, 10 or 11) is included in the immunogenic compositions of the invention, this is usually because certain antigens in the composition are most effective when adsorbed to the surface of such adjuvants (particularly aluminium hydroxide).

An advantage of the immunogenic compositions of the invention is that the presence of the polyanionic polymer (unlike regular anionic salts) does not cause significant desorption of antigens that are specifically adsorbed onto the above adjuvant (i.e. with a zero-point charge greater than 8). By not causing "significant desorption" it is typically meant that more than 50, 60, 70, 80 or, preferably, 90% of antigen that has been specifically adsorbed (i.e. intentionally adsorbed and/or adsorbed in a separate adsorption step before mixing with other vaccine components) onto the adjuvant remain adsorbed to the adjuvant after 15 minutes or 1 hour of adding the polyanionic polymer to the immunogenic composition of the invention. In general it is preferred that in so doing sufficient antigen remains adsorbed onto the adjuvant in order for the anti-antigen GMT titre in (µg/mL) in an appropriate model [e.g. mouse or rat, or in a well-conducted human clinical trial] to be more than 50, 60, 70, 80, 90, or 95% of the GMT titre of the antigen in the same immunogenic composition without polyanionic polymer in the same model.

Typically one or more of the following antigens may be present in the immunogenic composition of the invention and may have been specifically (and preferably individually) adsorbed onto an adjuvant with a zero point charge more than 8 (preferably aluminium hydroxide) before mixing with the other components of the immunogenic composition of the invention: diphtheria toxoid, tetanus toxoid, pertussis toxoid, FHA and pertactin (PRN). Preferably at least PRN is adsorbed onto aluminium hydroxide, and most preferably all 5 of the components are adsorbed onto aluminium hydroxide.

Methods of adsorbing DTPa and DTPw antigens onto aluminium adjuvants are known in the art. See for example WO 93/24148 and WO 97/00697. Usually components adsorbed onto adjuvant are left for a period of at least 10 minutes at room temperature at an appropriate pH for adsorbing most and preferably all of the antigen before mixing the antigens together in the combination immunogenic compositions of the present invention.

Other components are preferably unadsorbed (such as IPV) or adsorbed specifically onto other adjuvants—Hepatitis B surface antigen (HepBsa) being preferably adsorbed onto aluminium phosphate (as described in WO 93/24148) before mixing with other components.

Typical combination vaccines of the invention comprise: DTPa IPV HepBsa PRP (preferably conjugated to TT) PLG; DTPa IPV HepBsa PLG PRP MenC and/or MenY (where the capsular saccharides are preferably conjugated to TT). As mentioned above, PLG may reduce aggregation events which reduce the immunogenicity of meningococcal capsular saccharide epitopes in certain vaccines. Such combinations of the invention may comprise: DTPw HepBsa PLG Hib MenA and/or MenC (wherein the capsular saccharides are preferably conjugated to TT).

In a preferred embodiment, a vaccine is provided comprising the immunogenic composition of the invention and a pharmaceutically acceptable excipient. The pH of the vaccines of the present invention is usually between pH6-7, preferably pH 6.1.

Vaccine preparation is generally described in Vaccine Design—The Subunit and adjuvant approach Ed Powell and Newman; Pellum Press. Advantageously the combination vaccine according to the invention is a paediatric vaccine.

The amount of polysaccharide or oligosaccharide conjugate antigen in each vaccine dose is selected as an amount which induces an immunoprotective response without significant, adverse side effects in typical vaccinees. Such amount will vary depending on which specific immunogens are employed. Generally it is expected that each dose will comprise 1-1000 μg of conjugated polysaccharide or oligosaccharide (expressed in amount of saccharide), preferably 2-100 μg, more preferably 4-40, 2-15, or 3-10 μg, most preferably around or exactly 5 μg.

The content of protein antigens in the vaccine will typically be in the range 1-100 μg, preferably 5-50 μg, most typically in the range 5-25 μg.

An optimal amount of antigen for a particular vaccine can be ascertained by standard studies involving observation of antibody titres and other responses in subjects. Following an initial vaccination, subjects may receive one or two booster injections at about 4 weeks intervals or longer.

The vaccine preparations of the present invention may be used to protect or treat a mammal (preferably human) susceptible to infection, by means of administering said vaccine via systemic or mucosal route. These administrations may include injection via the intramuscular, intraperitoneal, intradermal or subcutaneous routes; or (less preferred) via mucosal administration to the oral/alimentary, respiratory, genitourinary tracts.

There is further provided a method of preventing or treating H. influenzae B disease (or disease associated with antigen of low pI of the invention) by administering a pharmaceutically effective amount of the vaccine of the invention to a patient in need thereof, and a use of the immunogenic composition or vaccine of the invention in the manufacture of a medicament for the prevention or treatment of H. influenzae B disease.

The present invention additionally provides a method for reducing the immunological interference and/or flocculation of a Haemophilus influenzae B capsular polysaccharide or oligosaccharide (PRP), which is preferably conjugated, in a combination vaccine (a vaccine of the invention comprising PRP and at least one further antigen) comprising one or more further antigens adsorbed to an adjuvant with a zero point charge greater than 8 (as described above, preferably aluminium hydroxide), wherein such method comprises the steps of:
 (i) adsorbing the one or more further antigens onto the adjuvant;
 (ii) adding a polyanionic polymer to said one or more further antigens; and
 (iii) then adding an immunogenic composition comprising PRP to said one or more further antigens;
or comprising the steps of:
 (i) adsorbing the one or more further antigens onto the adjuvant; and
 (ii) adding an immunogenic composition of the invention comprising PRP and a polyanionic polymer to said one or more further antigens.

In the former the adjuvant is policed before PRP is added, in the latter PRP is protected before it is added to the adjuvant. Preferably, in either method the components are mixed extemporaneously. The immunogenic composition comprising PRP is preferably lyophilised for greatest stability, most preferably in the presence of a stabilizing excipient (as described above). The immunogenic composition comprising PRP is preferably combined with one or more conjugated meningococcal capsular oligosaccharides or polysaccharides and/or one or more conjugated pneumococcal capsular oligosaccharides or polysaccharides (as described above).

Preferably the one or more further antigens adsorbed to adjuvant are selected from diphtheria toxoid, tetanus toxoid, pertussis toxoid, FHA and pertactin, most preferably all, as described above. Most preferably, as described above, the presence of the polyanionic polymer in the combination vaccine does not cause significant desorption of the one or more further antigens adsorbed to the adjuvant.

Further provided is a use of a polyanionic polymer (as described above) in an immunogenic composition further comprising a Haemophilus influenzae B capsular polysaccharide or oligosaccharide (PRP), preferably conjugated, as a means for protecting the immune response of PRP. By protecting the immune response it is meant retaining more than 50, 60, 70, 80, 90, or 95% of the anti-PRP GMT titre of the PRP component by itself, regardless of whether the immunogenic composition is later combined with a vaccine comprising adjuvant with a zero-point charge greater than 8 (as described above).

A kit is further provided comprising: i) a first immunogenic composition comprising a Haemophilus influenzae B capsular polysaccharide or oligosaccharide (PRP), preferably conjugated, and a polyanionic polymer (as described above); and ii) a second immunogenic composition comprising one or more antigens adsorbed onto an adjuvant with a zero point charge greater than 8 (preferably aluminium hydroxide). Preferably, the first immunogenic composition is lyophilised and further comprises a stabilizing excipient (as described above), preferably sucrose, and the second immunogenic composition is liquid. It is envisaged the contents of the kit may be simply administered by extemporaneously reconstituting the first immunogenic composition with the second immunogenic composition, and administering the resulting mixed composition. It is highly preferred that the polyanionic polymers of the present invention can dissolve in aqueous solution faster than PRP or PRP conjugates so that, when co-lyophilised, the polymer (such as PLG) may effectively protect the slower dissolving PRP when it is reconstituted in a liquid composition comprising an adjuvant with a zero point charge greater than 8.

Preferably the first immunogenic composition further comprises one or more conjugated meningococcal capsular oligosaccharides or polysaccharides selected from a group consisting of: MenC, MenY, MenA and MenW (e.g. A+C, A+Y, A+W, C+Y, C+W, Y+W, A+C+Y, A+C+W, A+Y+W, C+Y+W, A+C+Y+W), preferably MenC and/or MenY, and/or one or more conjugated pneumococcal capsular oligosaccharides or polysaccharides (as described above). Preferably, the second immunogenic composition comprises one or more (most preferably all) antigens selected from a group consisting of: diphtheria toxoid, tetanus toxoid, pertussis toxoid, FHA and pertactin. It may alternatively comprise DTPw.

As described above, all embodiments herein concerning PRP may equally (and alternatively) extend to other antigens or saccharides of low pI, whilst still taking advantage of the benefits of the invention (for instance the reduction or prevention of flocculation/aggregation events).

Further provided is the use of a polyanionic polymer of the invention in the manufacture of an immunogenic composition for the prevention of aggregation or flocculation occurring in said composition. Preferably the immunogenic composition is an immunogenic composition of the invention, e.g. one as hereinbefore described.

The following examples illustrate, but do not the limit the scope of, the invention.

EXAMPLES

Example 1

Numerous experiments were done with PRP polysaccharide conjugated to tetanus toxoid (PRP-T) in conjunction with PLG (Hib-PLG) experimental lots. The following parameters were evaluated:
  the molecular weight and content of PLG,
  the content of PRP-T,
  the stabiliser for the lyophilisation.
The following results are from the in-vitro, pre-clinical and potency testing of these experimental lots.
Results with the Experimental Lots
  In-Vitro Data with Hib-PLG
  Three types of mixing steps were followed to demonstrate the efficacy of PLG in reducing the physical interaction between PRP-T and Al(OH)$_3$, including mixing the commercially available INFANRIX PENTA™ (DTPaHepBIPV) vaccine with Hib-PLG vaccine:
  Step 1: pre-saturation whereby PLG was first adsorbed on Al(OH)$_3$, then PRP-T was added.
  Step 2: competition whereby PLG was put in competition with PRP-T for adsorption on Al(OH)$_3$
  INFANRIX PENTA™ Hib-PLG: whereby PLG and PRP-T were co-lyophilized and then put in competition for adsorption in INFANRIX PENTA™ vaccine, containing 500 µg Al(OH)$_3$ In all 3 steps, PLG was able to avoid flocculation induced by PRP-T (see FIGS. 1 and 2).

The 200 µM PLG (Mw 2,200) content was selected for clinical formulation as:
  no flocculation was observed,
  close to 80% PRP-T was non-adsorbed (according to the Dionex test)
  PLG is fully adsorbed
  all major components of INFANRIX® (DT, TT, PT, FHA, PRN [or 69K], IPV and HB surface antigen) were not affected.
  Both lactose and sucrose were found to be efficient cryoprotectors.

In FIG. 1 pre-saturation of Al(OH)$_3$ with PLG (106 residues) is shown. 10 µg PRP/dose, 500 µg AlOH. It was also found that 2000 uM PLG (Mw 1043—8 residues) could keep 80% of PRP-T in the supernatant (10 µg PRP/dose, 500 µg AlOH) with no flocculation resulting.

FIG. 2 shows the competition between PRP-T and PLG (85 residues). 100 µM PLG Mw 10,900 are able to limit adsorption of 10 µg Hib on 50 (to mimic hypothetical free Al(OH)$_3$ in INFANRIX PENTA™) as well as on 500 µg Al(OH)$_3$ (=full Al(OH)$_3$ dose in INFANRIX PENTA™).

In addition, 500 µm PLG Mw 2,178 (17 residues) are able to limit adsorption of 10 µg Hib on Al(OH)$_3$ after reconstitution of [Hib-PLG] cake with INFANRIX PENTA™ (1 h contact, then centrifugation 6 min 6500 g and dosage of Hib in supernatant by ELISA PRR'P-TT or Dionex dosage), as can 75 µM PLG Mw 10,900 (85 residues).

PLG Mw 2,178 (17 residues) is able to limit adsorption of 5 µg Hib (PRP-T) on Al(OH)$_3$ after reconstitution of [Hib-PLG] cake with INFANRIX PENTA™ (1 h contact, then centrifugation 6 min 6500 g and dosage of Hib in supernatant by ELISA PRR'P-TT or Dionex dosage)—175 and 200 µM were optimal concentrations in that there is an absence of flocculation and INFANRIX® antigen adsorption is retained.

PLG Mw 10,800 (85 residues) is able to limit adsorption of 5 µg Hib (amount of PRP in PRP-T) on Al(OH)$_3$ after reconstitution of [Hib-PLG] cake with INFANRIX PENTA™ (1 h contact, then centrifugation 6 min 6500 g and dosage of Hib in supernatant by ELISA PRR'P-TT or Dionex dosage)—30 and 35 µM were optimal concentrations in that there is an absence of flocculation and INFANRIX® antigen adsorption is retained.

Pre-Clinical Immunogenicity Data with Hib-PLG

Hib-PLG experimental formulations were evaluated in a rabbit model of immunogenicity and a baby rat model allowing evaluation of the Hib (PRP-T conjugate) immune interference induced by combination of INFANRIX PENTA™ a and Hib vaccines. Moreover, impact of Hib-PLG on the efficacy of INFANRIX PENTA™ was evaluated in a *B. pertussis* lung colonization murine model.

Rabbit Model of Immunogenicity
Study Design

In this model, 5 week old New Zealand female rabbits were intramuscularly immunised three times at two weeks intervals (day 0, 14, 28) with ¼ of a vaccine human dose. A sample size of 10 animals per group was used. Blood samples were taken on day 21, 28, and 42. Anti-PRP antibodies were measure by ELISA and are expressed in µg/ml.

Vaccines Administered

Formulations of PRP-T (5 µg PRP) containing high (10900 MW) and low (2200 MW) molecular weight PLG were evaluated in two concentrations. A similar Hib formulation but without PLG was included as control. See below for details of vaccines administered by group.

| Group | Vaccine |
| --- | --- |
| 1 | Hib (5 μg) PLG HMW (10900) 30 μM |
| 2 | Hib (5 μg) PLG HMW (10900) 70 μM |
| 3 | Hib (5 μg) PLG LMW (2200) 175 μM |
| 4 | Hib (5 μg) PLG LMW (2200) 450 μM |
| 5 | Hib (5 μg) |
| 6 | PLG HMW (10900) 40μ |

Figure 3:
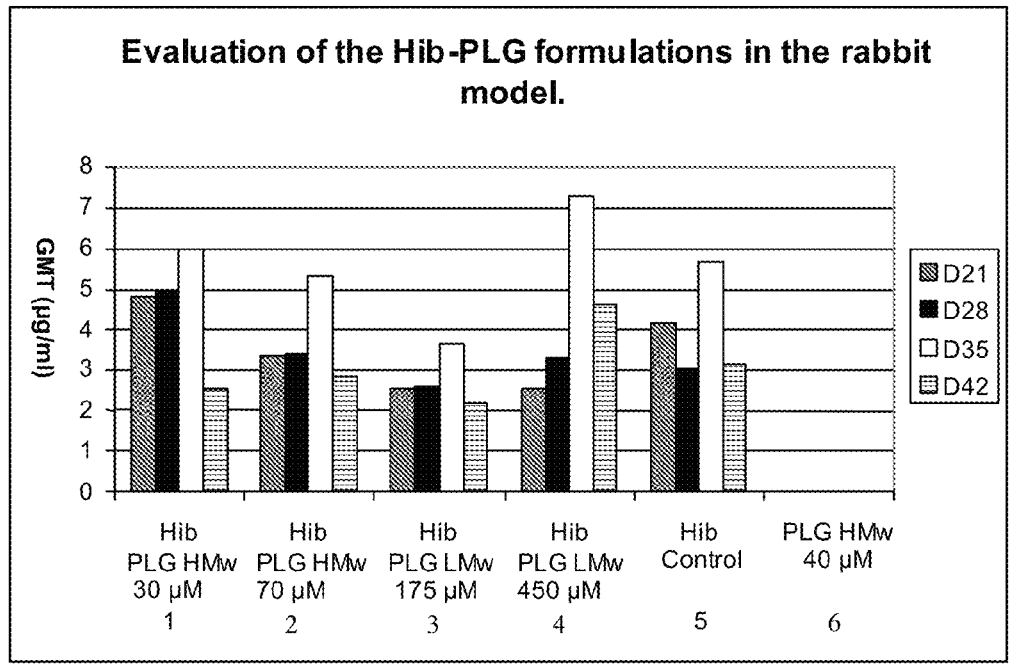
FIG. 3: Evaluation of the Hib-PLG formulations in the rabbit model.

Results
See FIG. 3.

Although some variability of PRP response can be observed in this rabbit model, no significant difference was demonstrated between groups.

There was a slight reduction of immunogenicity observed in rabbits having received Hib-PLG L Mw 175 μM, but all other formulations induced anti-PRP antibody levels similar to the Hib control group without addition of PLG.

No induction of anti-PLG antibodies after immunization of rabbits with these Hib-PLG experimental formulations were demonstrated.

Baby Rat Model of Hib Interference
Study Design

Seven day old OFA rats were intramuscularly immunised three times at two weeks intervals (day 0, 14, 28) with ⅒ of a vaccine human 0.5 mL dose. An equal repartition of male and female rats was realised. A sample size of 20 animals per group was used. Blood samples were realised on day 35 and anti-PRP antibodies were measured by ELISA and expressed in μg/ml.

Vaccines Administered

As a control of interference in the baby rat model, Hib combined with INFANRIX PENTA™ (10 μg PRP) was administered as well as Hib (10 μg) co-administered with INFANRIX PENTA™.

Hib (5 μg) formulated alone or containing various amounts of PLG were evaluated after reconstitution with INFANRIX PENTA™.

See below for details of vaccines administered by group

| Group | Vaccine |
| --- | --- |
| 1 | Hib (10 μg) + INFANRIX PENTA ™ |
| 2 | Hib (10 μg) reconstituted with INFANRIX PENTA ™ |
| 3 | Hib (5 μg) PLG HMW (10900) 30 μM reconstituted with INFANRIX PENTA ™ |
| 4 | Hib (5 μg) PLG HMW (10900) 75 μM reconstituted with INFANRIX PENTA ™ |
| 5 | Hib (5 μg) PLG LMW (2200) 175 μM reconstituted with INFANRIX PENTA ™ |
| 6 | Hib (5 μg) PLG LMW (2200) 500 μM reconstituted with INFANRIX PENTA ™ |
| 7 | Hib (5 μg) reconstituted with INFANRIX PENTA ™ |

Figure 4:
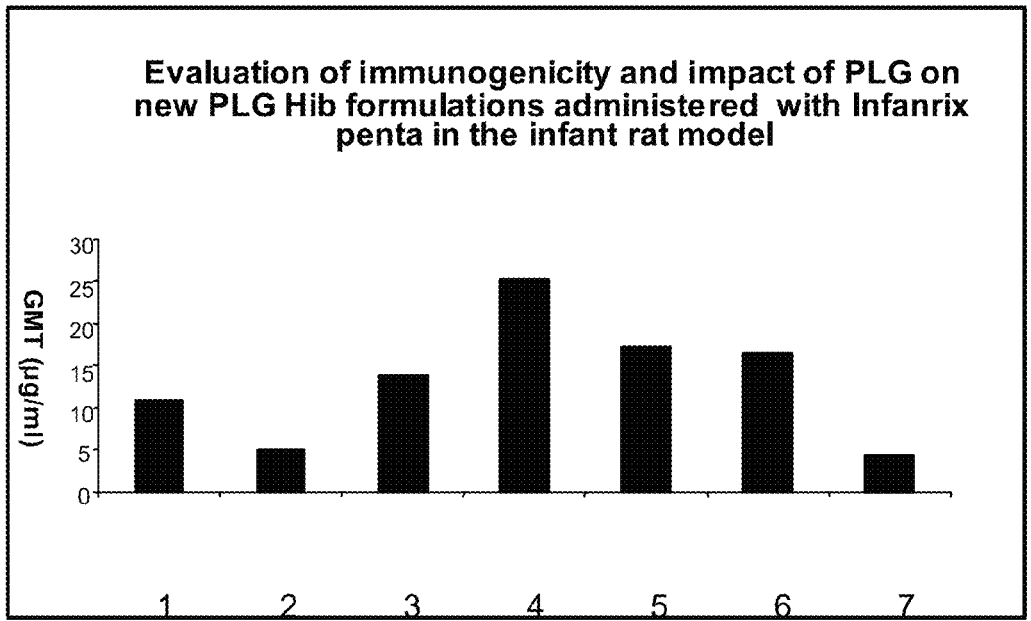
FIG. 4: Evaluation of immunogenicity and impact of PLG on new PLG Hib formulations administered with INFANRIX PENTA™ in the infant rat model.

Results
See FIG. 4.

When Hib is administered with INFANRIX PENTA™ immune interference was observed as compared with Hib co-administered separately with INFANRIX PENTA™.

The presence of PLG in Hib formulations resulted in partial or total restoration of the anti-Hib response. Indeed, a higher immune response against PRP was observed in all Hib-formulations containing PLG compared to the control group (Group 7).

These results demonstrate that prevention of Hib interaction with adsorption on Al(OH)$_3$ by addition of PLG can restore high anti-PRP antibody titres elicited by monovalent Hib vaccine.

No induction of anti-PLG antibodies after immunization of baby rats with these Hib-PLG experimental formulations were demonstrated.

Maintenance of Adsorption of Antigens on Aluminium Hydroxide

5 μg (saccharide) of PRP-T (Hib) was combined with different amounts of PLG (Sigma) of Mw 2,600 to realise either 0, 175 or 200 μM final concentration in the reconstituted vaccine. The samples were lyophilised in the presence of sucrose. The samples were then reconstituted with INFANRIX PENTA™ and after 1 hour the recovery of unadsorbed antigen in the supernatant (s/n) was measured. The results were as below:

|  | Control (0 PLG) | PLG 175 μM | PLG 200 μM |
| --- | --- | --- | --- |
| Flocculation? | Yes | No | No |
| % Hib in s/n | 0 | 0 | 0 |
| % DT in s/n | 0 | 1 | 4 |
| % TT in s/n | 0 | 8 | 17 |
| % PT in s/n | 3 | 3 | 3 |
| % FHA in s/n | 0 | 0 | 0 |
| % 69K (PRN) in s/n | 0 | 11 | 15 |
| % HepBsa in s/n | 1 | 1 | 1 |
| % IPV type I in s/n | 5 | 5 | 17 |
| % IPV type II in s/n | 5 | 5 | 5 |
| % IPV type III in s/n | 5 | 38 | 54 |

Conclusion:

Antigens that should be beneficially adsorbed to AlOH adjuvant (TT and pertactin) are maintained to a great extent in an adsorbed state. IPV type III seems most sensitive to desorption, however it is adsorbed to some degree. Also it should be noted IPV antigens are not specifically adsorbed to adjuvant before combination with the other antigens; rather IPV is mixed with the other antigens in an unadsorbed state. Interestingly in this experiment Hib seems to be fully adsorbed onto the adjuvant, but the PLG still prevents flocculation events (and Hib immune interference) from occurring. Typically the adjuvant is not saturated with PLG at 200 μM (290 μg/ml), and becomes saturated (free PLG beginning to be present in solution) only at concentrations of around 650 μg/ml at which point the PRP is around 60% free in solution. The PLG vaccines pass potency QC release criteria including pertussis challenge tests.

Example 2

Analysis of [DTPw/MenACHib] Combinations by Optical Microscopy

Figure 9:
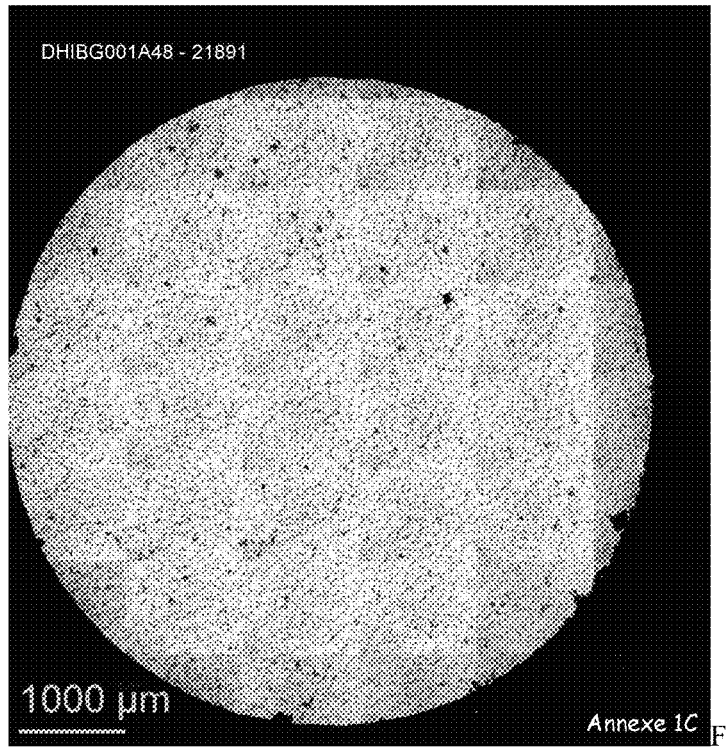
FIG. 9: Optical microscope picture showing no flocculation in the presence of 200 μM PLG Mw 2,200 (Sigma).
Figure 10:
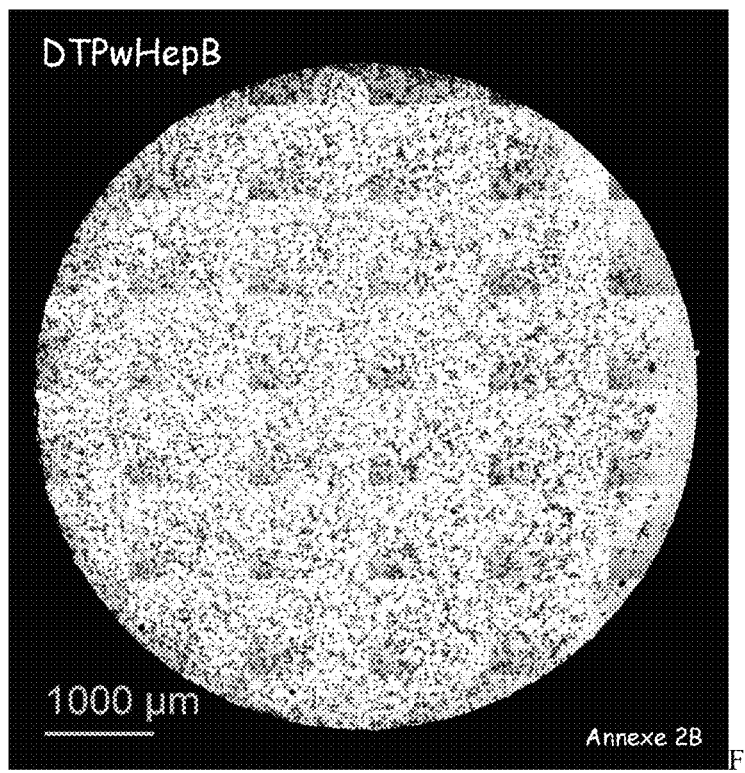
FIG. 10: Optical microscope picture showing no observable flocculations in DTPw controls.

The reconstitution of DTPaHepB IPV with Hib conjugate induces flocculation of the aluminium contained in DTPaHepB IPV (see FIG. 5). These may be observed visually and by optical microscopy, and may be measured by size and sedimentation analysis. FIG. 7 shows an optical microscope picture of INFANRIX PENTA™ (DTPaHepBIPV). FIG. 8 shows the sample flocculating when 5 μg saccharide of PRP-TT is added to the sample. FIG. 9 shows that no flocculation occurs in the presence of 200 μM PLG Mw 2,200 (Sigma).

This example sought to discover whether MenACHib-TT polysaccharide conjugates induce the apparition of aluminium flocculation when mixed with DTPwHB vaccines, and whether PLG could alleviate this.

Methods and Materials

The DTPaHepB IPV (INFANRIX®) tested had 500 μg Al(OH)$_3$, 200 μg AlPO$_4$ per human dose. The DTPwHepB (TRITANRIX™) tested had 260 μg Al(OH)$_3$, 370 μg AlPO$_4$ per human dose. PRP-TT (Hib) was unadjuvanted, as were the MenA-TT and MenC-TT capsular polysaccharide conjugates. 5 µg saccharide of the conjugates per dose were used in all experiments.

Analysis was by optical microscopy coupled to an image analyzer (KS400 system). DTPw samples were mixed with MenACHib samples comprising PLG for 15 minutes before observation.

Results

Flocculations were not observed in DTPw controls (FIG. 10) but were observed in DTPw samples with reconstituted MenACHib-TT (FIG. 11). MenACHib-TT alone does not flocculate.

Electrostatic interactions between polyanionic MenA, MenC and Hib polysaccharide conjugates and cationic Al(OH)$_3$ are probably the reason for this phenomenon (FIG. 5).

Figure 12:
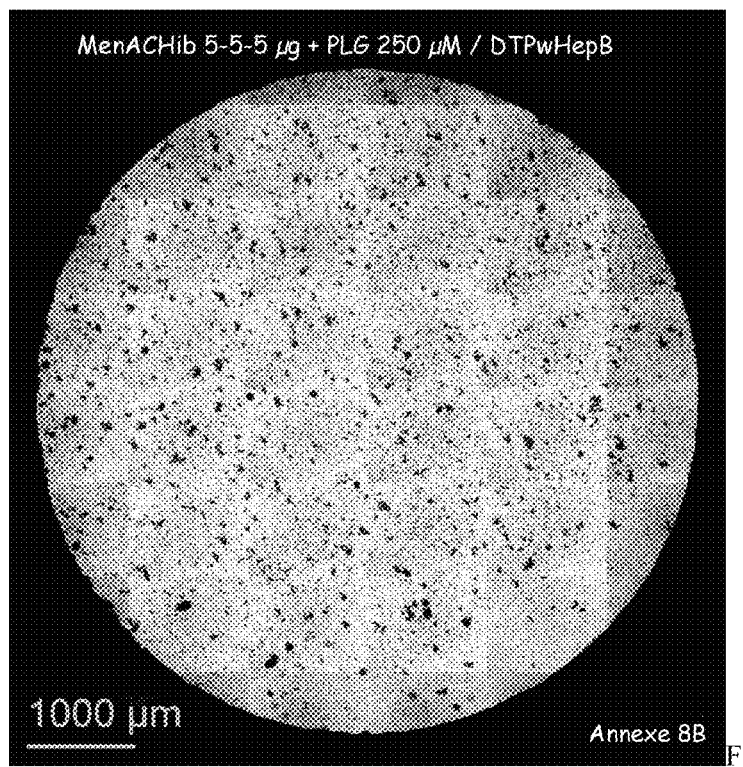
FIG. 12: Optical microscope picture showing that DTPwHepB/MenACHib with 250 μM PLG exhibits reduced flocculation.

Flocculation may be reduced by the addition of a competitive polyanionic excipient e.g. PLG. FIG. 12 shows that DTP-wHepB/MenACHib with 250 µM PLG exhibits reduced flocculation.

Conclusions

MenACHib-TT conjugates can induce aluminium flocculation in [DTPw/MenACHib] combinations. This may be reduced by the addition of a competitive polyanionic excipient.

Example 3

A Phase II, Randomized, Partially Blinded Clinical Trial to Evaluate the Immunogenicity and Reactogenicity of GSK Biologicals' Combined DTPa-HBV-IPV/Hib Vaccine (New Formulation with PLG) as Compared to GSK Biologicals' Licensed DTPa-HBV-IPV/Hib Vaccine (INFANRIX HEXA™) and to the Concomitant Administration of GSK Biologicals' Licensed DTPa-HBV-IPV (INFANRIX PENTA™) and Hib (HIBERIX™®) Vaccines, when Given as a Primary Vaccination to Healthy Infants at 2, 3 and 4 months of age The study was conducted at 9 centres in Poland.
Objectives:
Primary:
To evaluate the immunogenicity of DTPa-HBV-IPV/Hib (new formulation with PLG) in terms of anti-PRP antibody response in comparison with Hib (HIBERIX™®) co-administered with DTPa-HBV-IPV (INFANRIX PENTA™) and in comparison with DTPa-HBV-IPV/Hib (INFANRIX HEXA™, licensed formulation) one month after a three-dose primary vaccination course.
Secondary:
To evaluate the immunogenicity of DTPa-HBV-IPV/Hib (new formulation with PLG) in terms of antibody response to all other vaccine antigens in comparison with Hib co-administered with DTPa-HBV-IPV and in comparison with DTPa-HBV-IPV/Hib (licensed formulation) one month after a three-dose primary vaccination course.

To evaluate the immune response to Poly L Glutamate (PLG) in terms of antibody detection and concentration one month after a three-dose primary vaccination course.

To assess the safety and reactogenicity of the study vaccines in terms of solicited symptoms, unsolicited symptoms and serious adverse events (SAEs).

Study Design:
Partially blinded, randomized study with three parallel groups:
DTPa-HBV-IPV/Hib (new formulation with PLG)
DTPa-HBV-IPV/Hib (licensed formulation)
DTPa-HBV-IPV+Hib (licensed formulations)

The study was conducted in a single-blind manner with respect to the groups receiving DTPa-HBV-IPV/Hib (new formulation with PLG) and DTPa-HBV-IPV/Hib (licensed formulation). The group who received two separate injections (DTPa-HBV-IPV+Hib) was open.

Three doses of each vaccine were administered intramuscularly according to a 0, 1-month schedule to healthy infants who were 2 months of age at the time of the first dose (FIG. 6). Two blood samples (at 2 and 5 months of age) were taken from each subject.

Number of Subjects:
Completed:
149 (49 in group DTPa-HBV-IPV/Hib (new formulation), 50 in group DTPa-HBV-IPV/Hib (licensed formulation), 50 in group DTPa-HBV-IPV+Hib)
Safety:
Total vaccinated cohort: 150 (49 in group DTPa-HBV-IPV/Hib (new formulation), 50 in group DTPa-HBV-IPV/Hib (licensed formulation), 51 in group DTPa-HBV-IPV+Hib)
Immunogenicity:
ATP Cohort: 147 (48 in group DTPa-HBV-IPV/Hib (new formulation), 49 in group DTPa-HBV-IPV/Hib (licensed formulation), 50 in group DTPa-HBV-IPV+Hib)

Diagnosis and Criteria for Inclusion:
Infants born after a normal gestation period of 36-42 weeks, 8-12 weeks of age at the time of the first vaccine dose, free of obvious health problems as established by medical history and clinical examination before study entry, and with written informed consent obtained from parents or guardians of the subject.

Study Vaccine, Dose, Mode of Administration:
Vaccination Schedule/Site:
Each of the study vaccines was administered at 2, 3 and 4 months of age. The vaccines were administered as a single intramuscular injection in the left thigh for the *Haemophilus influenzae* type b vaccine and the right thigh for all other vaccines.

To prepare the DTPa-HBV-IPV/Hib vaccine (new formulation and licensed formulation), the liquid DTPa-HBV-IPV vaccine was reconstituted with the respective Hib vaccine. The *Haemophilus influenzae* type b vaccine was reconstituted with the supplied saline diluent.

Vaccine Composition/Dose:
One dose of GSK Biologicals' DTPa-HBV-IPV/Hib vaccine (new formulation) consisted of:
DTPa-HBV-IPV Component:
Diphtheria toxoid ≥30 IU (25 Lf), tetanus toxoid 40 IU (10 Lf), pertussis toxoid (PT) 25 µg, filamentous hemagglutinin (FHA) 25 µg, pertactin (PRN) 8 µg, hepatitis B surface antigen (recombinant) 10 µg, polioviruses type 1: 40 D antigen units, type 2: 8 D antigen units, type 3: 32 D antigen units, aluminium salts 0.7 mg, 2-phenoxyethanol ≤2.5 mg, sodium chloride 150 mM, formalin ≤100 µg, neomycin sulphate ≤25 µg and polysorbate ≤50 µg.
Hib Component:
Polyribosylribitol phosphate (PRP) 5 µg, tetanus toxoid 10-20 µg, saccharose 2.52% and poly L glutamate 200 µM [290 µg/ml] (Mw 2,200, 17 residues).

One dose of GSK Biologicals' DTPa-HBV-IPV/Hib vaccine (licensed formulation) consisted of:

DTPa-HBV-IPV Component:

Diphtheria toxoid ≥30 IU (25 Lf), tetanus toxoid ≥40 IU (10 Lf), pertussis toxoid (PT) 25 µg, filamentous hemagglutinin (FHA) 25 µg, pertactin (PRN) 8 µg, hepatitis B surface antigen (recombinant) 10 µg, polioviruses type 1: 40 D antigen units, type 2: 8 D antigen units, type 3: 32 D antigen units, aluminium salts 0.7 mg, 2-phenoxyethanol ≤2.5 mg, sodium chloride 150 mM, formalin ≤100 µg, neomycin sulphate ≤25 µg and polysorbate ≤50 µg.

Hib Component:

Polyribosylribitol phosphate (PRP) 10 µg, tetanus toxoid 20-40 µg, aluminium 0.12 mg and lactose 12.6 mg.

One dose of GSK Biologicals' DTPa-HBV-IPV vaccine consisted of:

Diphtheria toxoid ≥30 IU (25 Lf), tetanus toxoid ≥40 IU (10 Lf), pertussis toxoid (PT) 25 µg, filamentous hemagglutinin (FHA) 25 µg, pertactin (PRN) 8 µg, hepatitis B surface antigen (recombinant) 10 µg, polioviruses type 1: 40 D antigen units, type 2: 8 D antigen units, type 3: 32 D antigen units, aluminium salts 0.7 mg, 2-phenoxyethanol ≤2.5 mg, sodium chloride 150 mM, formalin ≤100 µg, neomycin sulphate ≤25 µg and polysorbate ≤50 µg.

One dose of GSK Biologicals' *Haemophilus influenzae* type b vaccine consisted of: Polyribosylribitol phosphate (PRP) 10 µg, tetanus toxoid 20-40 µg and lactose 10.08 mg.

Criteria for Evaluation:

Immunogenicity:

Primary Endpoint

Anti-PRP antibody concentrations one month after the three dose primary vaccination course.

Secondary Endpoint

Immunogenicity:

One month after the three-dose primary vaccination course,

Seroprotection status for the vaccine antigens were as follows:

Anti-PRP antibody concentrations ≥0.15 µg/ml and ≥1.0 µg/ml

Anti-HBs antibody concentrations ≥10 mIU/ml

Anti-diphtheria toxoid antibody concentrations ≥0.1 IU/ml

Anti-tetanus toxoid antibody concentrations ≥0.1 IU/ml

Anti-poliovirus type 1 antibody titres ≥8

Anti-poliovirus type 2 antibody titres ≥8

Anti-poliovirus type 3 antibody titres ≥8

Anti-PT, anti-FHA and anti-PRN seropositivity rates (antibody concentrations ≥5 EL·U/ml).

Anti-PT, anti-FHA, anti-PRN, anti-diphtheria and anti-tetanus toxoids, anti-poliovirus types 1, 2 and 3, and anti-HBs antibody concentrations.

Vaccine response rates to PT, FHA and PRN, defined as appearance of antibodies in subjects who were seronegative at pre-vaccination time point (i.e. with antibody concentrations <5 EL·U/ml) or at least maintenance of pre-vaccination antibody concentrations in subjects who were seropositive at pre-vaccination time point (i.e. with antibody concentrations ≥5 EL·U/ml), taking into consideration the decreasing maternal antibodies.

Anti-PLG antibody detection and concentration.

Safety:

Recording of solicited symptoms (pain, redness, swelling, drowsiness, fever, irritability/fussiness, loss of appetite) during the 4-day follow-up period (Day 0-Day 3) after each study vaccination. Recording of unsolicited symptoms occurring from Day 0 to Day 30 after each study vaccination and serious adverse events (SAE) during the entire study period.

Occurrence of solicited local symptoms during the 4-day follow-up period (Day 0-Day 3) after vaccination.

Occurrence of solicited general symptoms during the 4-day follow-up period (Day 0-Day 3) after vaccination.

Occurrence of unsolicited symptoms during the 31-day follow-up period (Day 0-Day 30) after vaccination.

Occurrence of serious adverse events (SAEs) during the entire study.

Statistical Methods:

Analysis of Immunogenicity:

The immunogenicity analysis was performed on the ATP cohort.

The following analyses has been performed for each treatment group at each time-point a serological result was available: Geometric mean antibody concentrations/titers (GMCs/GMTs) with 95% confidence intervals (CIs) were tabulated for anti-PRP and for antibodies against each vaccine antigen. Seropositivity/seroprotection rates with exact 95% CIs were tabulated. Vaccine response rates (post-dose 3) to pertussis antigens and their exact 95% CI was tabulated and the distribution of antibody concentrations/titers for each antigen post-dose 3 was displayed using reverse cumulative distribution curves.

The immunogenicity of the DTPa-HBV-IPV/Hib (new formulation with PLG) vaccine was compared with that of the licensed vaccines by computing both the 95% CI for the group GMC/GMT ratio for each antigen one month after the third vaccine dose and the standardized asymptotic 95% CI for the difference in seroprotection/seropositivity rates for each antigen one month after the third vaccine dose.

Analysis of Safety:

The safety analysis was performed on the Total vaccinated cohort. Within groups, the incidence of each solicited symptom that occurred within 4 days after vaccination was determined per group by tabulating the percentage of doses with the symptom and its exact 95% CI both at each dose and over the three doses for all groups and by tabulating the percentage of subjects with the symptom and its exact 95% CI for all groups. The percentage of subjects with unsolicited symptoms with its exact 95% CI was tabulated by group and by WHO preferred term and similar tabulation was done for grade "3" unsolicited symptoms and for unsolicited symptoms possible related to vaccination. In addition, the number of subjects who experienced at least one Serious Adverse Event (SAE) during the entire study period was reported. A two-sided p-value from the Fisher exact test and the standardized asymptotic 95% CIs for the differences between DTPa-HBV-IPV/Hib (new formulation) and each of the control groups were computed for the percentage of subjects with a given symptom of any intensity within 4 days after vaccination as well as for the percentage of subjects with rectal fever >39.0° C. within 4 days after vaccination and the percentage of subjects who received antipyretics within 4 days after vaccination.

Immunogenicity Results:

The immune response to PRP after vaccination with DTPa-HBV-IPV/Hib PLG was similar to that to HIBERIX® (HIB vaccine) and statistically higher than the response to INFANRIX HEXA™ (DTPa-HBV-IPV/Hib vaccine) (p<0.05), both in terms of GMCs and of seroprotection rates (Table 1).

The immune response to all the antigen components of the vaccine were similar in terms of seroprotection rates, for diphtheria, tetanus, hepatitis an poliovirus and in terms vaccine response rates to pertussis antigens (Table 2).

TABLE 1 response to the PRP antigen in the three study groups ((ATP cohort for immunogenicity)

| | | | ≥0.15 µg/ml | | | ≥1 µg/ml | | | | GMC (µg/ml) | | |
|---|---|---|---|---|---|---|---|---|---|---|---|---|
| | | | | | 95% CI | | | 95% CI | | | 95% CI | |
| Group | Timing | N | n | % | LL | UL | n | % | LL | UL | Value | LL | UL |
| DTPa-HBV-IPV/HibPLG | PRE | 48 | 17 | 35.4 | 22.2 | 50.5 | 1 | 2.1 | 0.1 | 11.1 | 0.137 | 0.106 | 0.179 |
| | PIII | 47 | 47 | 100.0 | 92.5 | 100.0 | 36 | 76.6 | 62.0 | 87.7 | 3.375 | 2.314 | 4.924 |
| DTPa-HBV-IPV/Hib | PRE | 49 | 18 | 36.7 | 23.4 | 51.7 | 6 | 12.2 | 4.6 | 24.8 | 0.177 | 0.122 | 0.255 |
| | PIII | 49 | 42 | 85.7 | 72.8 | 94.1 | 29 | 59.2 | 44.2 | 73.0 | 1.164 | 0.711 | 1.904 |
| DTPa-HBV-IPV + | PRE | 50 | 17 | 34.0 | 21.2 | 48.8 | 4 | 8.0 | 2.2 | 19.2 | 0.153 | 0.112 | 0.209 |
| HIBERIX ® | PIII | 50 | 48 | 96.0 | 86.3 | 99.5 | 36 | 72.0 | 57.5 | 83.8 | 3.014 | 1.846 | 4.920 |

N: number of subjects with available results
%: percentage of subjects with anti-PRP concentration above the specified cut-off
95% CI; LL, UL: 95% confidence interval; lower and upper limit

TABLE 2

Percentage of subjects seroprotected and vaccine response to pertussis antigens after primart vaccination (ATP cohort for immunogenicity)

| | DTPa-HBV-IPV/HibPLG | | | | DTPa-HBV-IPV/Hib | | | | DTPa-HBV-IPV + HIBERIX ® | | | |
|---|---|---|---|---|---|---|---|---|---|---|---|---|
| | | | 95% CI | | | | 95% CI | | | | 95% CI | |
| | N | % | LL | UL | N | % | LL | UL | N | % | LL | UL |
| Seroprotection | | | | | | | | | | | | |
| Anti-D (≥0.1 IU/ml) | 48 | 97.9 | 88.9 | 99.9 | 49 | 100 | 92.7 | 100 | 50 | 100 | 92.9 | 100 |
| Anti-T (≥0.1 IU/ml) | 47 | 100 | 92.5 | 100 | 49 | 100 | 92.7 | 100 | 50 | 100 | 92.9 | 100 |
| Anti-HBs (≥10 mIU/ml) | 47 | 100 | 92.5 | 100 | 49 | 100 | 92.7 | 100 | 50 | 98.0 | 89.4 | 99.9 |
| Anti-polio 1 (≥8) | 33 | 100 | 89.4 | 100 | 41 | 100 | 91.4 | 100 | 41 | 100 | 91.4 | 100 |
| Anti-polio 2 (≥8) | 34 | 100 | 89.7 | 100 | 39 | 97.4 | 86.5 | 99.9 | 36 | 100 | 90.3 | 100 |
| Anti-polio 3 (≥8) | 32 | 100 | 89.1 | 100 | 34 | 100 | 89.7 | 100 | 33 | 100 | 89.4 | 100 |
| Vaccine response | | | | | | | | | | | | |
| Anti-PT | 48 | 100 | 92.6 | 100 | 48 | 97.9 | 88.9 | 99.9 | 48 | 93.8 | 82.8 | 98.7 |
| Anti-FHA | 48 | 89.6 | 77.3 | 96.5 | 49 | 93.9 | 83.1 | 98.7 | 50 | 90.0 | 78.2 | 96.7 |
| Anti-PRN | 48 | 91.7 | 80 | 97.7 | 49 | 95.9 | 86 | 99.5 | 50 | 90.0 | 78.2 | 96.7 |

N: number of subjects with available results
%: percentage of subjects seroprotected or with vaccine response
95% CI; LL, UL: 95% confidence interval; lower and upper limit Safety Results:

The incidences of any local or general symptom were comparable between the three study groups. Incidences were not increased in the group receiving DTPa-HBV-IPV/HibPLG as compared with the other three study groups. Fever (rectal temperature) above 39.5° C. was not reported in any of the groups. Fever (rectal temperature) above 39.0° C. was not reported in the DTPa-HBV-IPV/HibPLG group.

TABLE 3

Safety results for the ATP safety cohort.

| | | DTPa-HBV-PV/HibPLG (N = 49) | | | | DTPa-HBV-IPV/Hib (N = 50) | | | | DTPa-HBV-IPV + HIBERIX ® (N = 51) | | | |
|---|---|---|---|---|---|---|---|---|---|---|---|---|---|
| | Intensity | n | % | 95% CI | | n | % | 95% CI | | n | % | 95% CI | |
| Solicited focal symptoms | | | | | | | | | | | | | |
| Pain | Any | 19 | 38.8 | 25.2 | 53.8 | 17 | 34.0 | 21.2 | 48.8 | 20 | 39.2 | 25.8 | 53.9 |
| | Grade "3" | 0 | 0.0 | 0.0 | 7.3 | 1 | 2.0 | 0.1 | 10.6 | 2 | 3.9 | 0.5 | 13.5 |
| Redness | Any | 27 | 55.1 | 40.2 | 69.3 | 26 | 52.0 | 37.4 | 66.3 | 23 | 45.1 | 31.1 | 59.7 |
| | >20 mm | 1 | 2.0 | 0.1 | 10.9 | 4 | 8.0 | 2.2 | 19.2 | 4 | 7.8 | 2.2 | 18.9 |
| Swelling | Any | 20 | 40.8 | 27.0 | 55.8 | 17 | 34.0 | 21.2 | 48.8 | 20 | 39.2 | 25.8 | 53.9 |
| | >20 mm | 6 | 12.2 | 4.6 | 24.8 | 5 | 10.0 | 3.3 | 21.8 | 11 | 21.6 | 11.3 | 35.3 |
| Solicited general symptoms: | | | | | | | | | | | | | |
| Drowsiness | Any | 22 | 44.9 | 30.7 | 59.8 | 26 | 52.0 | 37.4 | 66.3 | 26 | 51.0 | 36.6 | 65.2 |
| | Grade "3" | 1 | 2.0 | 0.1 | 10.9 | 1 | 2.0 | 0.1 | 10.6 | 0 | 0.0 | 0.0 | 7.0 |
| | Related | 22 | 44.9 | 30.7 | 59.8 | 24 | 48.0 | 33.7 | 62.6 | 24 | 47.1 | 32.9 | 61.5 |

TABLE 3-continued

Safety results for the ATP safety cohort.

| | | DTPa-HBV-PV/HibPLG (N = 49) | | | | DTPa-HBV-IPV/Hib (N = 50) | | | | DTPa-HBV-IPV + HIBERIX ® (N = 51) | | | |
|---|---|---|---|---|---|---|---|---|---|---|---|---|---|
| | Intensity | n | % | 95% CI | | n | % | 95% CI | | n | % | 95% CI | |
| Irritability | Any | 29 | 59.2 | 44.2 | 73.0 | 30 | 60.0 | 45.2 | 73.6 | 30 | 58.8 | 44.2 | 72.4 |
| | Grade "3" | 4 | 8.2 | 2.3 | 19.6 | 1 | 2.0 | 0.1 | 10.6 | 3 | 5.9 | 1.2 | 16.2 |
| | Related | 28 | 57.1 | 42.2 | 71.2 | 28 | 56.0 | 41.3 | 70.0 | 29 | 56.9 | 42.2 | 70.7 |
| Loss of appetite | Any | 17 | 34.7 | 21.7 | 49.6 | 16 | 32.0 | 19.5 | 46.7 | 14 | 27.5 | 15.9 | 41.7 |
| | Grade "3" | 0 | 0.0 | 0.0 | 7.3 | 0 | 0.0 | 0.0 | 7.1 | 0 | 0.0 | 0.0 | 7.0 |
| | Related | 17 | 34.7 | 21.7 | 49.6 | 13 | 26.0 | 14.6 | 40.3 | 12 | 23.5 | 12.8 | 37.5 |
| Fever | ≥38° C. | 7 | 14.3 | 5.9 | 27.2 | 8 | 16.0 | 7.2 | 29.1 | 8 | 15.7 | 7.0 | 28.6 |
| | >38.5° C. | 2 | 10.5 | 3.4 | 22.2 | 8 | 16.0 | 7.2 | 29.1 | 7 | 13.7 | 5.7 | 26.3 |
| | >39° C. | 0 | 0.0 | 0.0 | 7.3 | 0 | 0.0 | 0.0 | 7.1 | 2 | 3.9 | 0.5 | 13.5 |
| | >39.5° C. | 0 | 0.0 | 0.0 | 7.3 | 0 | 0.0 | 0.0 | 7.1 | 0 | 0.0 | 0.0 | 7.0 |
| | Related | 5 | 10.2 | 3.4 | 22.2 | 8 | 16.0 | 7.2 | 29.1 | 7 | 13.7 | 5.7 | 26.3 |

Serious Adverse Events:

Eleven SAEs were reported during the course of the study. None of these was causally related to vaccination by the investigator.

Conclusion(s):

The Hib response after vaccination with DTPa-HBV-IPV/HibPLG was significantly higher as compared to DTPa-HBV-IPV/Hib and was not different from that to the standalone Hib conjugate vaccine HIBERIX®. There was thus no observed Hib immune interference problem with the new formulation.

The response to the other antigens administered was similar to that to DTPa-HBV-IPV/Hib and to DTPa-HBV-IPV in terms of seroprotection rates and vaccine responses. The other antigens seem to be compatible with PLG as a vaccine excipient. Although GMC titres against pertactin and IPV type I fell for DTPa-HBV-IPV/HibPLG as compared with DTPa-HBV-IPV/Hib (they were, however, more similar to the titres for the DTPa-HBV-IPV+Hib group) the vaccine response to pertactin and the seroprotection rates for IPV type I for all vaccines were comparable.

The DTPa-HBV-IPV/HibPLG showed a reactogenicity comparable to that of the DTPa-HBV-IPV/Hib vaccine.

We claim:

1. A method of reducing flocculation in an immunogenic composition, where said immunogenic composition comprises (a) *Haemophilus influenzae* B capsular polysaccharide or oligosaccharide (PRP) and (b) at least one non-PRP antigen, said method comprising the steps of:
   (i) providing a first composition comprising a non-PRP antigen adsorbed onto an adjuvant with a zero point charge greater than 8;
   (ii) adding to said first composition poly-L-glutamic acid (PLG) or poly-L-aspartic acid (PLA) or a salt thereof, to provide a second composition; and
   (iii) adding *Haemophilus influenzae* B capsular polysaccharide or oligosaccharide (PRP) to said second composition to provide a final immunogenic composition.

2. The method of claim 1, where said PRP is conjugated to a carrier protein.

3. The method of claim 2, where said carrier protein is a source of T-helper cell epitopes.

4. The method of claim 2, where said carrier protein is selected from the group consisting of tetanus toxoid, diphtheria toxoid, CRM197, and protein D.

5. The method of claim 1, where said adjuvant is aluminum hydroxide.

6. The method of claim 1, wherein the non-PRP antigen is selected from tetanus toxoid and diphtheria toxoid.

7. The method of claim 1, wherein the non-PRP antigen is a *B. Pertussis* antigen selected from pertussis toxoid (PT), filamentous hemagglutinin (FHA), pertactin (PRN).

8. The method of claim 1, wherein the final immunogenic composition comprises a conjugate of a carrier protein and a meningococcal capsular oligosaccharide or polysaccharide selected from a group consisting of MenC, MenY, MenA and MenW.

9. The method of claim 8 wherein the carrier protein is selected from the group consisting of tetanus toxoid, diphtheria toxoid, CRM197, and protein D.

10. The method of claim 1, wherein the final immunogenic composition comprises a conjugate of a carrier protein and a pneumococcal capsular oligosaccharide or polysaccharide.

11. The method of claim 10, wherein the carrier protein is selected from the group consisting of tetanus toxoid, diphtheria toxoid, CRM197, and protein D.

12. The method of claim 1, wherein the final immunogenic composition comprises unadsorbed Inactivated Polio Vaccine (IPV).

13. The method of claim 1, wherein the final immunogenic composition comprises Hepatitis B surface antigen adsorbed onto aluminium phosphate.

14. The method of claim 1, further comprising lyophilizing said final immunogenic composition, where said lyophilized composition comprises a stabilizing excipient selected from the group consisting of glucose, maltulose, iso-maltulose, lactulose, sucrose, sorbitol, maltose, lactose, iso-maltose, maltitol, lactitol, palatinit, trehalose, raffinose, stachyose, and melezitose.

15. The method of claim 14, where said stabilizing excipient is sucrose.

16. A method of reducing flocculation in an immunogenic composition, where said immunogenic composition comprises (a) *Haemophilus influenzae* B capsular polysaccharide or oligosaccharide (PRP) and (b) at least one non-PRP antigen, said method comprising the steps of:
   (i) providing a first composition comprising a non-PRP antigen adsorbed onto an adjuvant with a zero point charge greater than 8;
   (ii) adding to said first composition a second composition comprising *Haemophilus influenzae* B capsular polysaccharide or oligosaccharide (PRP) and poly-L-glutamic acid (PLG) or poly-L-aspartic acid (PLA) or a salt thereof, to provide a final immunogenic composition.

17. The method of claim 16, where said PRP is conjugated to a carrier protein.

18. The method of claim 17, where said carrier protein is a source of T-helper cell epitopes.

19. The method of claim 17, where said carrier protein is selected from the group consisting of tetanus toxoid, diphtheria toxoid, CRM197, and protein D.

20. The method of claim 19, where said adjuvant is aluminum hydroxide.

21. The method of claim 16, wherein the non-PRP antigen is selected from tetanus toxoid and diphtheria toxoid.

22. The method of claim 16, wherein the non-PRP antigen is a *B. Pertussis* antigen selected from pertussis toxoid (PT), filamentous hemagglutinin (FHA), pertactin (PRN), agglutinogen 2 and agglutinogen 3.

23. The method of claim 16, wherein the final immunogenic composition comprises a conjugate of a carrier protein and a meningococcal capsular oligosaccharide or polysaccharide selected from a group consisting of MenC, MenY, MenA and MenW.

24. The method of claim 23 wherein the carrier protein is selected from the group consisting of tetanus toxoid, diphtheria toxoid, CRM197, and protein D.

25. The method of claim 16, wherein the final immunogenic composition comprises a conjugate of a carrier protein and a pneumococcal capsular oligosaccharide or polysaccharide.

26. The method of claim 25, wherein the carrier protein is selected from the group consisting of tetanus toxoid, diphtheria toxoid, CRM197, and protein D.

27. The method of claim 16, wherein the final immunogenic composition comprises unadsorbed Inactivated Polio Vaccine (IPV).

28. The method of claim 16, wherein the final immunogenic composition comprises Hepatitis B surface antigen adsorbed onto aluminium phosphate.

29. The method of claim 16, further comprising lyophilizing said final immunogenic composition, where said lyophilized composition comprises a stabilizing excipient selected from the group consisting of glucose, maltulose, iso-maltulose, lactulose, sucrose, sorbitol, maltose, lactose, iso-maltose, maltitol, lactitol, palatinit, trehalose, raffinose, stachyose, and melezitose.

30. The method of claim 29, where said stabilizing excipient is sucrose.

* * * * *